(12) United States Patent
Marion-Poll et al.

(10) Patent No.: US 8,304,603 B2
(45) Date of Patent: Nov. 6, 2012

(54) PLANTS WITH INCREASED TOLERANCE TO WATER DEFICIT

(75) Inventors: Annie Marion-Poll, Saint Cyr l'Ecole (FR); Helen North, Bois d'Arcy (FR); Philippe Lessard, Chamalieres (FR); Elise Redondo, Mirefleurs (FR)

(73) Assignee: Genoplante-Velor, Evry Cedex (FR)

( * ) Notice: Subject to any disclaimer, the term of this patent is extended or adjusted under 35 U.S.C. 154(b) by 564 days.

(21) Appl. No.: 12/304,876

(22) PCT Filed: Jun. 18, 2007

(86) PCT No.: PCT/IB2007/002785
§ 371 (c)(1),
(2), (4) Date: May 19, 2009

(87) PCT Pub. No.: WO2007/144775
PCT Pub. Date: Dec. 21, 2007

(65) Prior Publication Data
US 2009/0307796 A1     Dec. 10, 2009

(30) Foreign Application Priority Data
Jun. 16, 2006   (EP) .................................... 06290983

(51) Int. Cl.
*A01H 5/00*     (2006.01)
*C12N 15/63*    (2006.01)
*C12N 15/82*    (2006.01)

(52) U.S. Cl. ........ 800/278; 800/298; 435/468; 435/419; 435/320.1

(58) Field of Classification Search ........................ None
See application file for complete search history.

(56) References Cited

U.S. PATENT DOCUMENTS
2004/0034888 A1*  2/2004  Liu et al. ...................... 800/289
2004/0216190 A1* 10/2004  Kovalic ........................ 800/289

OTHER PUBLICATIONS

Gao et al—PNAS 2004 (101)25,9205-9210.*
Iuchi et al (The Plant Journal (2001) 24(4), 325-333.*
International Search Report and Written Opinion for PCT/IB2007/002785 filed Jun. 18, 2007.
Database UniProt Hypothetical protein P0408F06.3; Nov. 23, 2004; XP002407233.
Iuchi S et al.; "Regulation of drought tolerance by gene manipulation of 9-cis-eposycarotenoid dioxygenase, a key enzyme in abscisic acid biosynthesis in arabidopsis"; Plant Journal, Blackwell Scientific Publications, Oxford, GB; vol. 27, No. 4, 2001; pp. 325-333; XP002973637.

* cited by examiner

*Primary Examiner* — Anne Kubelik
*Assistant Examiner* — Lee A Visone
(74) *Attorney, Agent, or Firm* — Alston & Bird LLP

(57) ABSTRACT

The invention relates to a method for increasing the tolerance of a plant to water deficit, by overexpression in the plant of a protein, designated ABA4, which is involved in the conversion of violaxanthin to neoxanthin in the biosynthesis of abscisic acid.

14 Claims, 14 Drawing Sheets

Figure 3 (followed)

A

B

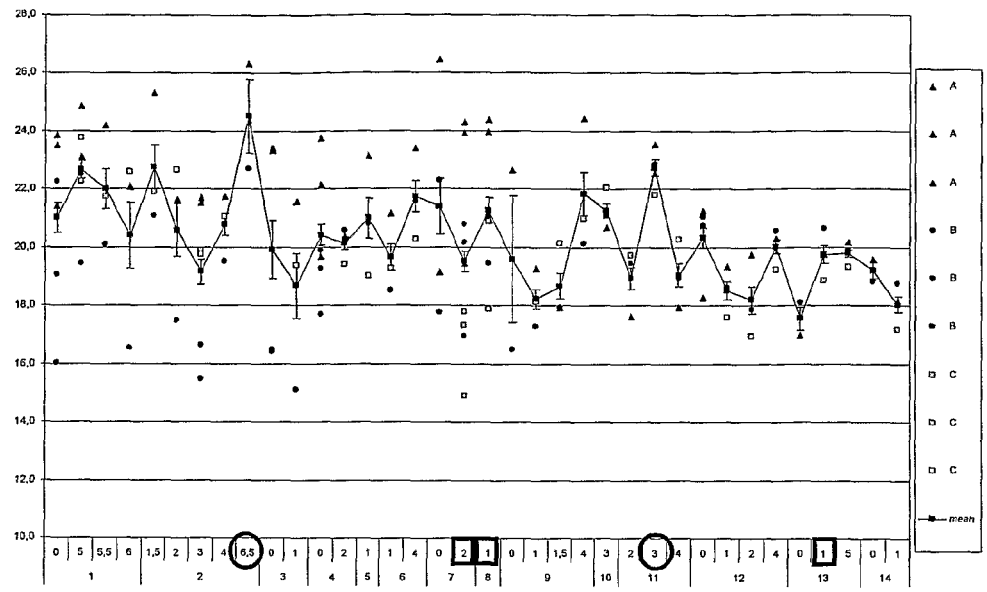
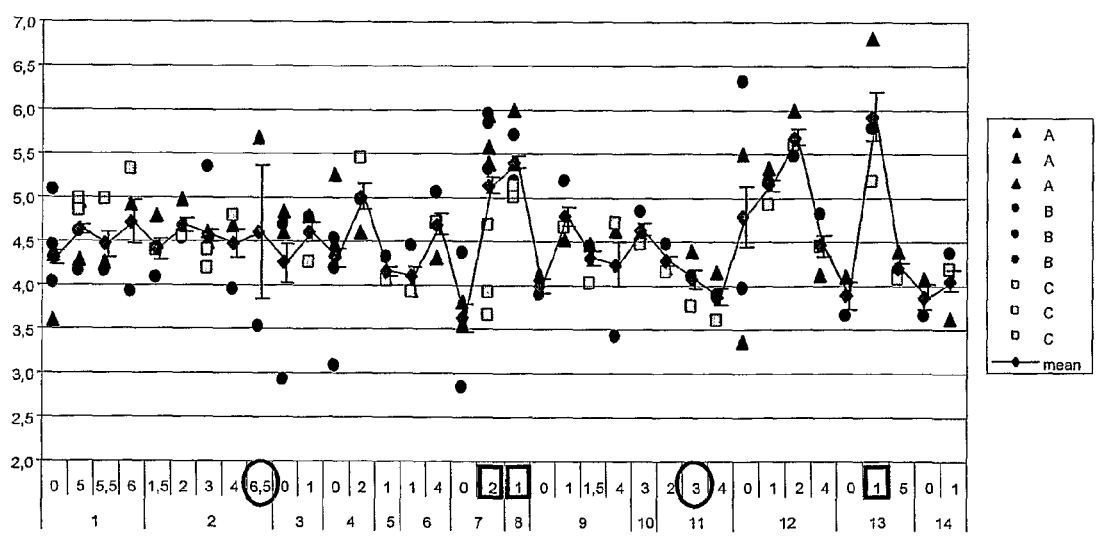
Figure 11 (followed)

RAA-002b

SEQUENCE LISTING

```
<160> NUMBER OF SEQ ID NOS: 38

<210> SEQ ID NO 1
<211> LENGTH: 1636
<212> TYPE: DNA
<213> ORGANISM: Arabidopsis thaliana
<220> FEATURE:
<221> NAME/KEY: exon
<222> LOCATION: (180)..(227)
<220> FEATURE:
<221> NAME/KEY: CDS
<222> LOCATION: (180)..(227)
<220> FEATURE:
<221> NAME/KEY: Intron
<222> LOCATION: (229)..(498)
<220> FEATURE:
<221> NAME/KEY: exon
<222> LOCATION: (499)..(661)
<220> FEATURE:
<221> NAME/KEY: CDS
<222> LOCATION: (499)..(661)
<220> FEATURE:
<221> NAME/KEY: Intron
<222> LOCATION: (662)..(767)
<220> FEATURE:
<221> NAME/KEY: exon
<222> LOCATION: (768)..(868)
<220> FEATURE:
<221> NAME/KEY: CDS
<222> LOCATION: (768)..(868)
<220> FEATURE:
<221> NAME/KEY: Intron
<222> LOCATION: (869)..(948)
<220> FEATURE:
<221> NAME/KEY: exon
<222> LOCATION: (949)..(1077)
<220> FEATURE:
<221> NAME/KEY: CDS
<222> LOCATION: (949)..(1077)
<220> FEATURE:
<221> NAME/KEY: Intron
<222> LOCATION: (1078)..(1149)
<220> FEATURE:
<221> NAME/KEY: exon
<222> LOCATION: (1150)..(1238)
<220> FEATURE:
<221> NAME/KEY: CDS
```

```
<222> LOCATION: (1150)..(1238)
<220> FEATURE:
<221> NAME/KEY: Intron
<222> LOCATION: (1239)..(1323)
<220> FEATURE:
<221> NAME/KEY: exon
<222> LOCATION: (1324)..(1456)
<220> FEATURE:
<221> NAME/KEY: CDS
<222> LOCATION: (1324)..(1453)

<400> SEQUENCE: 1
```

| | | |
|---|---|---|
| ataattgtcg acactgagca aagaaagagt gaaagacaac ttttttccct tccactttcg | 60 | |
| ttttttttta tccagtggaa atctcgcaac cattcccatt atatatatgc agagagtttg | 120 | |
| ttgaagaagg tgatgaaaga tcaattttg gcaattagtg gtgaagattt gaatcagag | 179 | |

```
atg ggt ttt tct tct ttc att tct cag cct ttg tct tca tct ctc tcg        227
Met Gly Phe Ser Ser Phe Ile Ser Gln Pro Leu Ser Ser Ser Leu Ser
1               5                  10                  15
```

| | |
|---|---|
| gtatcttctt cttctttaat ttcactatac atatatgtac agttgttgga ttagattctg | 287 |
| tgttgagtta aactatagtt atggataacc ttaaagtctt tttatctttt gactagaatt | 347 |
| gaagaattta atgggttttt gagttgactt tattctttct gagtcactgt tacagaatct | 407 |
| ctgttcttga ttgttgtgag tttttgtatg aaagtttctg aatttctatg aagtaaaaga | 467 |
| agaatctttc tttctttgtt ggtgaattca | 467 |

```
                                   g gtg atg aaa cgc aac gtt tct       519
                                     Val Met Lys Arg Asn Val Ser
                                                              20 gct aaa aga tcg gaa ctt tgt ctt gat tct tca aag att aga tta gat        567
Ala Lys Arg Ser Glu Leu Cys Leu Asp Ser Ser Lys Ile Arg Leu Asp
        25                  30                  35 cat cgt tgg agc ttc att gga gga tca aga atc tct gtt cag tcc aat        615
His Arg Trp Ser Phe Ile Gly Gly Ser Arg Ile Ser Val Gln Ser Asn
40                  45                  50                  55 tct tac acc gta gtt cac aag aaa ttc tcc ggt gta cga gct tca t          661
Ser Tyr Thr Val Val His Lys Lys Phe Ser Gly Val Arg Ala Ser
                    60                  65                  70
```

| | |
|---|---|
| gtactgtgtc tcataaccat ttaaagatta aactttgtca ctcatttgt gactttgatc | 721 |
| taagattata tgtgtgatta gaatctctta tatgttcatg ttgtag gg | 775 |

```
                                                     tta act          775
                                                     Trp Leu Thr act act cag att gca agc agt gta ttt gcg gtt gga act acc gcg gtt        823
Thr Thr Gln Ile Ala Ser Ser Val Phe Ala Val Gly Thr Thr Ala Val
    75                  80                  85 tta ccc ttc tat act cta atg gtt gta gca cca aaa gct gaa att           868
Leu Pro Phe Tyr Thr Leu Met Val Val Ala Pro Lys Ala Glu Ile
    90                  95                  100
```

| | |
|---|---|
| gtaagtttaa ttttgttgca agttttacaa cttgatgacc taatgaagtt gatcaaaatt | 928 |
| gagtatgttt ctttgtgcag | 981 |

```
                     acc aag aag tgt atg gag agt agc gta ccg tat       981
                     Thr Lys Lys Cys Met Glu Ser Ser Val Pro Tyr
                                 105                 110                 115 atc atc tta ggc gta tta tat gtg tat ttg tta tac att tct tgg aca       1029
Ile Ile Leu Gly Val Leu Tyr Val Tyr Leu Leu Tyr Ile Ser Trp Thr
            120                 125                 130 ccc gag acg ctc aaa tac atg ttt tct agt aaa tac atg ttg cca gag       1077
Pro Glu Thr Leu Lys Tyr Met Phe Ser Ser Lys Tyr Met Leu Pro Glu
    135                 140                 145
```

| | |
|---|---|
| gtttttgcttt cccttaacca tccacaatat ttgtatcatt gcagtttcta aagttagttt | 1137 |
| tttcatctgc ag | 1137 |

```
              ttg tct gga ata gct aaa atg ttc tca agt gaa atg act     1188
              Leu Ser Gly Ile Ala Lys Met Phe Ser Ser Glu Met Thr
                      150                 155                 160
```

```
ctt gct tct gct tgg att cat ctt ctt gtt gta gat ctt ttc gct gca      1236
Leu Ala Ser Ala Trp Ile His Leu Leu Val Val Asp Leu Phe Ala Ala
            165                 170                 175 cg  gtatattaca cttctcttct tctcaatggg ttctgaaatt atcctacatg            1288
Arg tttcttataa agcgtgtttt gggtttactc tgcag g caa gtt tat aat gat ggg      1342
                                        Gln Val Tyr Asn Asp Gly
                                                        180 tta gag aac cag atc gag acg agg cat tcg gtt tca ctt tgc ctt ctc      1390
Leu Glu Asn Gln Ile Glu Thr Arg His Ser Val Ser Leu Cys Leu Leu
        185                 190                 195 ttc tgt ccg gtt gga atc gtt tcg cat ttc gta acc aaa gct ata atc      1438
Phe Cys Pro Val Gly Ile Val Ser His Phe Val Thr Lys Ala Ile Ile
200                 205                 210                 215 aac aac cag tac aaa taa gctgatgatc ttggtttctt aaatgccat              1486
Asn Asn Gln Tyr Lys
                220 aaagatttgg aatgatgctt cattatgctt ttgctcatgt taaattagct gtaatgggtt    1546 aagttgttga cagtatcaat gagaccaaac aactcgagac aagttttcat cttttgtcaa    1606 taagtttacc tcatgaggtt tttgcagaaa                                     1636

<210> SEQ ID NO 2
<211> LENGTH: 220
<212> TYPE: PRT
<213> ORGANISM: Arabidopsis thaliana

<400> SEQUENCE: 2

Met Gly Phe Ser Ser Phe Ile Ser Gln Pro Leu Ser Ser Ser Leu Ser
1               5                   10                  15

Val Met Lys Arg Asn Val Ser Ala Lys Arg Ser Glu Leu Cys Leu Asp
            20                  25                  30

Ser Ser Lys Ile Arg Leu Asp His Arg Trp Ser Phe Ile Gly Gly Ser
        35                  40                  45

Arg Ile Ser Val Gln Ser Asn Ser Tyr Thr Val Val His Lys Lys Phe
    50                  55                  60

Ser Gly Val Arg Ala Ser Trp Leu Thr Thr Thr Gln Ile Ala Ser Ser
65                  70                  75                  80

Val Phe Ala Val Gly Thr Thr Ala Val Leu Pro Phe Tyr Thr Leu Met
                85                  90                  95

Val Val Ala Pro Lys Ala Glu Ile Thr Lys Lys Cys Met Glu Ser Ser
            100                 105                 110

Val Pro Tyr Ile Ile Leu Gly Val Leu Tyr Val Tyr Leu Leu Tyr Ile
        115                 120                 125

Ser Trp Thr Pro Glu Thr Leu Lys Tyr Met Phe Ser Lys Tyr Met
    130                 135                 140

Leu Pro Glu Leu Ser Gly Ile Ala Lys Met Phe Ser Glu Met Thr
145                 150                 155                 160

Leu Ala Ser Ala Trp Ile His Leu Leu Val Val Asp Leu Phe Ala Ala
                165                 170                 175

Arg Gln Val Tyr Asn Asp Gly Leu Glu Asn Gln Ile Glu Thr Arg His
            180                 185                 190

Ser Val Ser Leu Cys Leu Leu Phe Cys Pro Val Gly Ile Val Ser His
        195                 200                 205

Phe Val Thr Lys Ala Ile Ile Asn Asn Gln Tyr Lys
    210                 215                 220
```

```
<210> SEQ ID NO 3
<211> LENGTH: 4200
<212> TYPE: DNA
<213> ORGANISM: Zea mays
<220> FEATURE:
<221> NAME/KEY: exon
<222> LOCATION: (1970)..(2020)
<220> FEATURE:
<221> NAME/KEY: CDS
<222> LOCATION: (1970)..(2020)
<220> FEATURE:
<221> NAME/KEY: Intron
<222> LOCATION: (2021)..(2163)
<220> FEATURE:
<221> NAME/KEY: exon
<222> LOCATION: (2164)..(2362)
<220> FEATURE:
<221> NAME/KEY: CDS
<222> LOCATION: (2164)..(2362)
<220> FEATURE:
<221> NAME/KEY: Intron
<222> LOCATION: (2363)..(2499)
<220> FEATURE:
<221> NAME/KEY: exon
<222> LOCATION: (2500)..(2600)
<220> FEATURE:
<221> NAME/KEY: CDS
<222> LOCATION: (2500)..(2600)
<220> FEATURE:
<221> NAME/KEY: Intron
<222> LOCATION: (2601)..(2733)
<220> FEATURE:
<221> NAME/KEY: exon
<222> LOCATION: (2734)..(2862)
<220> FEATURE:
<221> NAME/KEY: CDS
<222> LOCATION: (2734)..(2862)
<220> FEATURE:
<221> NAME/KEY: Intron
<222> LOCATION: (2863)..(2967)
<220> FEATURE:
<221> NAME/KEY: exon
<222> LOCATION: (2968)..(3056)
<220> FEATURE:
<221> NAME/KEY: CDS
<222> LOCATION: (2968)..(3056)
<220> FEATURE:
<221> NAME/KEY: Intron
<222> LOCATION: (3057)..(3166)
<220> FEATURE:
<221> NAME/KEY: exon
<222> LOCATION: (3167)..(3305)
<220> FEATURE:
<221> NAME/KEY: CDS
<222> LOCATION: (3167)..(3302)

<400> SEQUENCE: 3
cgcgcagttc cacctgcctg aagagcagcc ttgtgggcat cgccctcgca gttgcagcta      60
gtctcgtgct atcatctccc gacatggacc ttccgctcga gtgggagaag atccaggcga     120
tggtctcatc gcacctgtcg ttctgaacat acctgtccag gatctccaga cgtgggtgga     180
tctaagtcat ggatggctga ctcagcagtg aagagagctc aacgggtggt gagaataagg     240
aggggggggg gggggtggat aggtggtaga accgaaaggt tacagttttc atgagtcgcc     300
attttttccc gcgcttcctc cagcagcagc ggtgcatggt aggagggaga tgcagtagtc     360
gactttgcag agagttggtt taatcggtag actggtgggt gcgaagaagg ttgagtcaaa     420
tggctcgacc agaggattaa cacctttgc ttttctcttt gtgcatctga gatgatgttg      480
gcaaacagtt ttggttatct agaatcttga atcgtattcc gtgatgtgtg cttgtcggct     540
acatgtatct gttgcgttga tatctgctta aattgtgtga tgctgtgccc atgtcagtat     600
gcttttgtca aagatctccc ttttcgcagg tgtggttcct ggtgttggaa cctactgttg     660
```

```
gtatctgttg cgttgatatc tgcttaaatt gcgttggtat ctgttgcgtt gatatctggg    720
tttgactgta tgtaacctac tgtttcttgg tggtgaggat gttaagggtt tcctttatgg    780
ccgattatct gcagtttatg tggaactgga ttagattaga cctgtttgac gtggttttt     840 cgggttgggt cagttttttg gcttttttag atcgtttttt tttttgtgtt tggtcggttttg   900 ggtcaataat catggcaacg tggatcaaaa ctatggtttg taattgtccg ttgtattgat    960
tgggttagat tgattttttt tcagagtgag tcatgttaga ttggtcgagt tagacagctc   1020
atattcagca tcatgttcgc tgatgtttgt tacgacttta atctggctgt gactacgact   1080
tctataatat tttgtcttta tgaattgtag ctgtagcagt ccgaatagct gtggttgtag   1140
gtctagacca ttgtcaatga ttgtattatg atttagcata ttttgtcaaa gatattttat    1200
gatctatatt gaatatgatg agttgatgat aggggaggag gcgaggtgaa cagctagctc   1260
tcatctgtcc atgatctacc gtatcatgta atagtggagc taaacatacg acaaaattt    1320 tggactcaga taccatgatc cagatccaga tattctttcc gtgcgggaaa tcatacgagc   1380
gaaggcgtgc ggactgcgga gcggatattc ctgggcgggg cggcgacgtg tcgaggcgga   1440
agcgccgcgc cggtggccaa gacgggggc agattgaaca cgggggaagg ggggtggccc    1500
tcgcttcgtc ccctgcacat ccgcacatgg ccttcgcttg actcgtgatg gaatggagtc   1560
accgccacca cgatgctggg ctggcgattg gtgcgcccgc ccacgcctcc agcgccgcca   1620
ccgcccaaat ccaacctcct ccggcgggcc cagccaccga cccgacccga cccgacccgc   1680
tcagcactag tgagcatggc aagtgctgtt ggcgagtggt tcaggtcgag gcgagtgctg   1740
ttggcactag tggctgctcg cctgcctggt gcctgcttga cagcttgagc aggggtcaga   1800
gcagctgctc ggaggccggc ctggcccgtc cctgggtgtg ctcgccactg tcgcagagtg   1860
ctcagtggaa cccgcggcac aaactacaaa gggacctgac tcgaatggca gctcgtcacc   1920
tctcccacct gtcctcccca gcgtctgctt cctcctcgg  cccgagcc atg gcg ccc   1978
                                             Met Ala Pro
                                              1 tgc gcg tcc ccg tcc gcc ctc gcg ctc tcc gcc agc acg cgg             2020
Cys Ala Ser Pro Ser Ala Leu Ala Leu Ser Ala Ser Thr Arg
  5              10                  15 gtaggttcgc cgttcgccag ccccaaccca acagcggcga ttttattcac cactgtcctg   2080
tatactctcc ctctcgtgtc tgccgtgctg tgcagctggt tgatttgctc tgcctcggcc   2140
tccgcctgac cgccttgctg cag gtc agc agc ttc cca ctg acg ctg cgc ccg   2193
                         Val Ser Ser Phe Pro Leu Thr Leu Arg Pro
                          20                  25 cgg ccg cgg ccg gag gcg cgt gtg ccg cgc gcg ccc ggc ggc gcc cag     2241
Arg Pro Arg Pro Glu Ala Arg Val Pro Arg Ala Pro Gly Gly Ala Gln
 30                  35                  40 ctc cgc ccg gcg acc gcg tgc tct tgg ccg cgc ccc ttg ctg ccc gag     2289
Leu Arg Pro Ala Thr Ala Cys Ser Trp Pro Arg Pro Leu Leu Pro Glu
 45                  50                  55 ctc gcg ccg gcg ttc cct cgt gcc ggc gcc cgc agc gcc ggc aga ccg     2337
Leu Ala Pro Ala Phe Pro Arg Ala Gly Ala Arg Ser Ala Gly Arg Pro
 60              65                  70                  75 cag ccg ctg ttc cgg ccc cgc gca a gtacgcacct tttcctttt                2382
Gln Pro Leu Phe Arg Pro Arg Ala
                  80 tcttttccgc gcttccttca gcagttcgat tctgctcaat cgaactatta cctgttcaag   2442 tttccccggc tgaaactgaa actgaattgt tcgcttccgg cgacaacaaa caaacag      2499 tg  atg acg acg tct cag atc gcc agc tgc gcc ttc acc gtg ggc acg     2546
    Met Met Thr Thr Ser Gln Ile Ala Ser Cys Ala Phe Thr Val Gly Thr
```

```
                    85                  90                  95
gtc gcc gtc ctc ccc ttc tac acg ctc atg gtc gtc gcc ccc aac gcc     2594
Val Ala Val Leu Pro Phe Tyr Thr Leu Met Val Val Ala Pro Asn Ala
100                 105                 110                 115 gac atc gtaagccaac ttcctctcct ccacacagtt taacggcaca cgaacacgac      2650
Asp Ile acgacacgac atggcgcttc tccatcaatc cacgcctcga tctctcctcg tcaccacgtc   2710
tccctgctct tggttgcgcg cag acc aaa cgc acg gtg gag agc agc gcc ccc   2763
                          Thr Lys Arg Thr Val Glu Ser Ser Ala Pro
                                      120                 125 tac gtc gcc cta ggc ctc ctc tac gcc tac ctg ctc tac ctg tct tgg     2811
Tyr Val Ala Leu Gly Leu Leu Tyr Ala Tyr Leu Leu Tyr Leu Ser Trp
        130                 135                 140 acc ccc gac acc ctt cgc gcc atg ttc gcg agc aag tac tgg ctc ccc     2859
Thr Pro Asp Thr Leu Arg Ala Met Phe Ala Ser Lys Tyr Trp Leu Pro
    145                 150                 155 gag gtactgctgc agcaccattt gctgaaacag ttacgcgctc tctgaatgtg          2912
Glu
160 tctgctgctg ttaaagatta agctgctgct aataggaatg ggatgcactt tgcag ctg    2970
                                                              Leu ccg ggc atc gtc agg atg ttc gcg agc gag atg acc gtc gcc tcc gca     3018
Pro Gly Ile Val Arg Met Phe Ala Ser Glu Met Thr Val Ala Ser Ala
            165                 170                 175 tgg atc cac ctc cta gca gtc gat ctc ttc gcg gcg ag  gtcaggcacc      3066
Trp Ile His Leu Leu Ala Val Asp Leu Phe Ala Ala Arg
        180                 185 actaaaccaa gtagtaccag ttctgcagtg ctgggactgg accaggggtg cgagggaacg   3126
cgtgctaaca agtgtgtgtg tgggtggatt tgtaatgcag g cag gtc tac cac gac   3182
                                              Gln Val Tyr His Asp
                                                              195 ggt ctc aag aac aac atc gag acc agg cat tcg gtc tcg ctg tgc ctg     3230
Gly Leu Lys Asn Asn Ile Glu Thr Arg His Ser Val Ser Leu Cys Leu
                    200                 205                 210 ctc ttc tgc ccg gtc ggg atc ctg gct cat gtg gta acc aag gta ttg     3278
Leu Phe Cys Pro Val Gly Ile Leu Ala His Val Val Thr Lys Val Leu
        215                 220                 225 gca ggg gca gct ggc cgc tca cat tga tgattggaat tgggtggttg           3325
Ala Gly Ala Ala Gly Arg Ser His
        230             235 tatctaggat tcccgttttg tttagctggt ggagtttatg agatctggat atgaataaag   3385
cttgttcaag gcactgattc tttcaatgtg gggtcacctt aaaggaaaga aattagttag   3445
acaaaaaaat agtttaaatt aattaaaggt agctaataac taataaaaaa attagttaca   3505
aattagtcta cttatcatcc aaactatcta gatgtactaa gggggtgttt aaatgcatta   3565 gagctaaatag ttagtggcta aaattagttg agaaacattc tagctaatag ttcaactatt  3625
agttattttt gctaaattag ttaatagtta ggtagctatt tgttagctag ctaatttcat   3685
taacaatttt tagtcaatta actattagtt ctagtgcatt taaacaccct ctaaagctaa   3745
tttttagcta actaacaatt acattctgta tcaaataaag gaaaaaacag tgacaacggt   3805
gtcattccgg accaatatca ataaaagttg accgttcatt gttagtgtga cccacccttg   3865
cattcatttg aaacgagacg agaacaaagt atctacaagt tggtcatcta gtaccactag   3925
gcgttagaat cacatgcatt ccatatagat cgaagtgaca ctcatgagag aaaacaaaaa   3985
ggtttatcga aacactgtaa aatgttaact agactctaac atgtttggca aaacatttga   4045
```

```
gggttagctc aattgagaag agagataaaa atactattgc cgctgattta cagagagcac    4105
tagacatgta caatgaggca ccatacatgg cacctaatat gaatacaacc tattttagtt    4165
cataattttc agttgagcac catggttttt cagtg                               4200
```

<210> SEQ ID NO 4
<211> LENGTH: 235
<212> TYPE: PRT
<213> ORGANISM: Zea mays

<400> SEQUENCE: 4

```
Met Ala Pro Cys Ala Ser Pro Ser Ala Leu Ala Leu Ser Ala Ser Thr
1               5                   10                  15

Arg Val Ser Ser Phe Pro Leu Thr Leu Arg Pro Arg Pro Arg Pro Glu
            20                  25                  30

Ala Arg Val Pro Arg Ala Pro Gly Gly Ala Gln Leu Arg Pro Ala Thr
        35                  40                  45

Ala Cys Ser Trp Pro Arg Pro Leu Leu Pro Glu Leu Ala Pro Ala Phe
    50                  55                  60

Pro Arg Ala Gly Ala Arg Ser Ala Gly Arg Pro Gln Pro Leu Phe Arg
65                  70                  75                  80

Pro Arg Ala Met Met Thr Thr Ser Gln Ile Ala Ser Cys Ala Phe Thr
                85                  90                  95

Val Gly Thr Val Ala Val Leu Pro Phe Tyr Thr Leu Met Val Val Ala
            100                 105                 110

Pro Asn Ala Asp Ile Thr Lys Arg Thr Val Glu Ser Ser Ala Pro Tyr
        115                 120                 125

Val Ala Leu Gly Leu Leu Tyr Ala Tyr Leu Leu Tyr Leu Ser Trp Thr
    130                 135                 140

Pro Asp Thr Leu Arg Ala Met Phe Ala Ser Lys Tyr Trp Leu Pro Glu
145                 150                 155                 160

Leu Pro Gly Ile Val Arg Met Phe Ala Ser Glu Met Thr Val Ala Ser
                165                 170                 175

Ala Trp Ile His Leu Leu Ala Val Asp Leu Phe Ala Ala Arg Gln Val
            180                 185                 190

Tyr His Asp Gly Leu Lys Asn Asn Ile Glu Thr Arg His Ser Val Ser
        195                 200                 205

Leu Cys Leu Leu Phe Cys Pro Val Gly Ile Leu Ala His Val Val Thr
    210                 215                 220

Lys Val Leu Ala Gly Ala Ala Gly Arg Ser His
225                 230                 235
```

<210> SEQ ID NO 5
<211> LENGTH: 2447
<212> TYPE: DNA
<213> ORGANISM: Zea mays
<220> FEATURE:
<221> NAME/KEY: exon
<222> LOCATION: (246)..(296)
<220> FEATURE:
<221> NAME/KEY: CDS
<222> LOCATION: (246)..(296)
<220> FEATURE:
<221> NAME/KEY: Intron
<222> LOCATION: (297)..(394)
<220> FEATURE:
<221> NAME/KEY: exon
<222> LOCATION: (395)..(584)
<220> FEATURE:
<221> NAME/KEY: CDS
<222> LOCATION: (395)..(584)
<220> FEATURE:

```
<221> NAME/KEY: Intron
<222> LOCATION: (585)..(665)
<220> FEATURE:
<221> NAME/KEY: exon
<222> LOCATION: (666)..(766)
<220> FEATURE:
<221> NAME/KEY: CDS
<222> LOCATION: (666)..(766)
<220> FEATURE:
<221> NAME/KEY: Intron
<222> LOCATION: (767)..(871)
<220> FEATURE:
<221> NAME/KEY: exon
<222> LOCATION: (872)..(1000)
<220> FEATURE:
<221> NAME/KEY: CDS
<222> LOCATION: (872)..(1000)
<220> FEATURE:
<221> NAME/KEY: Intron
<222> LOCATION: (1001)..(1088)
<220> FEATURE:
<221> NAME/KEY: exon
<222> LOCATION: (1089)..(1177)
<220> FEATURE:
<221> NAME/KEY: CDS
<222> LOCATION: (1089)..(1177)
<220> FEATURE:
<221> NAME/KEY: Intron
<222> LOCATION: (1178)..(1273)
<220> FEATURE:
<221> NAME/KEY: exon
<222> LOCATION: (1274)..(1412)
<220> FEATURE:
<221> NAME/KEY: CDS
<222> LOCATION: (1274)..(1409)

<400> SEQUENCE: 5
gcggaggacg gtgcgcccgc ccacgcgtcg agcgccacag acccgacgcg cccggcatgg      60
cagggcaagg cagccgcacg agccgcttct agcctgctgg tcggagtcgg agggccgggc     120
cagggctggg tgtggtcgcc actgttccag agtgcccagt ggtgccggct gccgcggtag     180
tacaaactac aaaggcaaag gggactcccc cgcgtccgct tccctcgccc cccagtccc      240 cagac atg gcg ccc tgc gcg tcc ccg tcc gcc ctc gcg ctc tcc gcc agc     290
      Met Ala Pro Cys Ala Ser Pro Ser Ala Leu Ala Leu Ser Ala Ser
      1               5                  10                  15 acg cgg gtaggtcgcc agccccaaca acggcgagaa ttcgccacta ccctctcgtg        346
Thr Arg tctgccgtgc gcagctggtt gatttgctct gcatctgcct tgctgcag gtc agc atc      403
                                                     Val Ser Ile
                                                             20 ctc cgg ctc ccg ctg gcg ctg cgg cag cgg gcg gag gcg cgc gtg ccc       451
Leu Arg Leu Pro Leu Ala Leu Arg Gln Arg Ala Glu Ala Arg Val Pro
              25                  30                  35 ggc gcc cag ttc cgc ccg tcg acc gcg tgc tcc tgg gcg cgc ccc ttg       499
Gly Ala Gln Phe Arg Pro Ser Thr Ala Cys Ser Trp Ala Arg Pro Leu
        40                  45                  50 ctg ccc gag ctc gcg ggg gcg gtc cct cgt gcc ggc gcc cgc ggc act       547
Leu Pro Glu Leu Ala Gly Ala Val Pro Arg Ala Gly Ala Arg Gly Thr
55                  60                  65 ggc agg agg acg cag ccg ctg ttc cgg cct cgc gca t gtacgctccc          594
Gly Arg Arg Thr Gln Pro Leu Phe Arg Pro Arg Ala
70                  75                  80 ttgaacagtt cgattttct cattcttcga actgtctgtg aaattgacct ggctgaaatt      654
gacattgaca g tg  acg acg acg tct cag att gcc agc tgc gcc ttc acc      703
              Leu Thr Thr Thr Ser Gln Ile Ala Ser Cys Ala Phe Thr
                                  85                  90 ctg ggc acg gtc gcc gtc ctc ccc ttc tac acc ctc atg gtc gtc gcc      751
```

```
Leu Gly Thr Val Ala Val Leu Pro Phe Tyr Thr Leu Met Val Val Ala
         95                  100                 105 ccc aac gcc gac atc gtgagccatc ttcctccgtc attcacaact taataactca    806
Pro Asn Ala Asp Ile
110 aggcatggag ctctctcgtc agtggtcacc acctcatgtc ctcatctccc tgctcctgcg    866 cgcag acc aaa cgc acc gtg gag agc ggc gct ccc tac gtc gcc ctg ggc    916
      Thr Lys Arg Thr Val Glu Ser Gly Ala Pro Tyr Val Ala Leu Gly
          115                 120                 125 ctc ctc tac gcc tac ctg ctc tac ctg tcc tgg acc ccc gac acc ctg      964
Leu Leu Tyr Ala Tyr Leu Leu Tyr Leu Ser Trp Thr Pro Asp Thr Leu
130                 135                 140                 145 cgc gcc atg ttc gct agc aag tac tgg ctc cct gag gtactgtgct          1010
Arg Ala Met Phe Ala Ser Lys Tyr Trp Leu Pro Glu
                150                 155 acgcgttgtc ccaatgttct gctgctgtta gctgctgctg ctagctgctc acagagatgg   1070
gatgggacga cttggcag ttg gcg ggc atc gtg agg atg ttc gcg agc gag     1121
                    Leu Ala Gly Ile Val Arg Met Phe Ala Ser Glu
                                    160                 165 atg acc gtc gcc tcc gcg tgg atc cac ctc cta gca gtc gac ctc ttc    1169
Met Thr Val Ala Ser Ala Trp Ile His Leu Leu Ala Val Asp Leu Phe
    170                 175                 180 gcg gca ag  gtcaggcacg caccactgaa ccaaccaacc aaccaagtag             1217
Ala Ala Arg
185 cagtgctggg actgagggggg acgcgtcgcg cgttttggtt tgggtttgca atgcag g   1274 cag gtg tac cac gac ggc ctc agg aac aac gtc gag acc agg cac tct    1322
Gln Val Tyr His Asp Gly Leu Arg Asn Asn Val Glu Thr Arg His Ser
    190                 195                 200 gtc tcg ctg tgc ctg ctc ttc tgc ccg gtt ggg atc ctg gct cat gtg    1370
Val Ser Leu Cys Leu Leu Phe Cys Pro Val Gly Ile Leu Ala His Val
    205                 210                 215 ctg acc aag gta ctg gca ggg gca gtt gcc cgc tca cac tga            1412
Leu Thr Lys Val Leu Ala Gly Ala Val Ala Arg Ser His
220                 225                 230 tgattgcaat tgggtggttg tattgtatct aggattcttc cattgttacc atgtggagat   1472
gtggattgag cggaattgat agggtttacc gtttgattca ccaaatgtaa cgtaaatgat   1532
aagagtaacg attcacactc gaataccggt ggtaataaat ttaataagg cggtatccat    1592
ttataatacg gttggactta acaaacgtt aaatcgttat actttggtaa tgtaatggta    1652
accgataacg ttaaatcatg tttgtttaag tccaaccggt atcgatatca tactacaaat   1712
gtataccgtc ttatttaaat ttattactac cagtattcga aggtgaatcg ttaccattac   1772
tatttacgtt acatttgatg aacaaaataa atcccaaaca agttaaattt tttaactttt   1832
tctaattcta ttcaatctat atgtaatagg aataaccgaa cgagccggtt ttatatgatc   1892
tggatatgaa taaaactggt ttaacgcacc gattcttgcc atgtgggctc gcctattttt   1952
tttcaaaaaa caaaaatgct gacagctgaa ttcacttacg ggatccattc attttgagt    2012
aattagaatt tatttaataa agtaatctat ttagtttgaa atttaacttt tcatcacttt   2072
ttcaaaattt agatataagt ctatctcaaa tttatgtgat aaaagatcag aaatgatttt   2132
ttataagtag aatttgtttt tactctataa tttatagaac gctcttcagc tcactcctct   2192
ataataaaaa tatagcacat aaatatcttc aatatctttc taccaatatt atacaaatat   2252
attttatata aaatcaaatt agattaatta atatatgctt aagttactac taaaatgaat   2312
tcaattctaa ggattcaaac atgactttat cgtctaggaa tttatagtat actattttag   2372
```

-continued

```
tgcccgtgcg ttgcaacggg aacatataat actatgatag ttatgagaaa atagttcttt    2432
tagaagagca acttc                                                     2447
```

<210> SEQ ID NO 6
<211> LENGTH: 232
<212> TYPE: PRT
<213> ORGANISM: Zea mays

<400> SEQUENCE: 6

```
Met Ala Pro Cys Ala Ser Pro Ser Ala Leu Ala Leu Ser Ala Ser Thr
1               5                   10                  15

Arg Val Ser Ile Leu Arg Leu Pro Leu Ala Leu Arg Gln Arg Ala Glu
            20                  25                  30

Ala Arg Val Pro Gly Ala Gln Phe Arg Pro Ser Thr Ala Cys Ser Trp
        35                  40                  45

Ala Arg Pro Leu Leu Pro Glu Leu Ala Gly Ala Val Pro Arg Ala Gly
    50                  55                  60

Ala Arg Gly Thr Gly Arg Arg Thr Gln Pro Leu Phe Arg Pro Arg Ala
65                  70                  75                  80

Leu Thr Thr Thr Ser Gln Ile Ala Ser Cys Ala Phe Thr Leu Gly Thr
                85                  90                  95

Val Ala Val Leu Pro Phe Tyr Thr Leu Met Val Val Ala Pro Asn Ala
            100                 105                 110

Asp Ile Thr Lys Arg Thr Val Glu Ser Gly Ala Pro Tyr Val Ala Leu
        115                 120                 125

Gly Leu Leu Tyr Ala Tyr Leu Leu Tyr Leu Ser Trp Thr Pro Asp Thr
    130                 135                 140

Leu Arg Ala Met Phe Ala Ser Lys Tyr Trp Leu Pro Glu Leu Ala Gly
145                 150                 155                 160

Ile Val Arg Met Phe Ala Ser Glu Met Thr Val Ala Ser Ala Trp Ile
                165                 170                 175

His Leu Leu Ala Val Asp Leu Phe Ala Ala Arg Gln Val Tyr His Asp
            180                 185                 190

Gly Leu Arg Asn Asn Val Glu Thr Arg His Ser Val Ser Leu Cys Leu
        195                 200                 205

Leu Phe Cys Pro Val Gly Ile Leu Ala His Val Leu Thr Lys Val Leu
    210                 215                 220

Ala Gly Ala Val Ala Arg Ser His
225                 230
```

<210> SEQ ID NO 7
<211> LENGTH: 1204
<212> TYPE: DNA
<213> ORGANISM: Oryza sp.
<220> FEATURE:
<221> NAME/KEY: exon
<222> LOCATION: (29)..(64)
<220> FEATURE:
<221> NAME/KEY: CDS
<222> LOCATION: (29)..(64)
<220> FEATURE:
<221> NAME/KEY: Intron
<222> LOCATION: (65)..(147)
<220> FEATURE:
<221> NAME/KEY: exon
<222> LOCATION: (148)..(340)
<220> FEATURE:
<221> NAME/KEY: CDS
<222> LOCATION: (148)..(340)
<220> FEATURE:
<221> NAME/KEY: Intron

```
<222> LOCATION: (341)..(439)
<220> FEATURE:
<221> NAME/KEY: exon
<222> LOCATION: (440)..(540)
<220> FEATURE:
<221> NAME/KEY: CDS
<222> LOCATION: (440)..(540)
<220> FEATURE:
<221> NAME/KEY: Intron
<222> LOCATION: (541)..(626)
<220> FEATURE:
<221> NAME/KEY: exon
<222> LOCATION: (627)..(755)
<220> FEATURE:
<221> NAME/KEY: CDS
<222> LOCATION: (627)..(755)
<220> FEATURE:
<221> NAME/KEY: Intron
<222> LOCATION: (756)..(834)
<220> FEATURE:
<221> NAME/KEY: exon
<222> LOCATION: (835)..(923)
<220> FEATURE:
<221> NAME/KEY: CDS
<222> LOCATION: (835)..(923)
<220> FEATURE:
<221> NAME/KEY: Intron
<222> LOCATION: (924)..(1036)
<220> FEATURE:
<221> NAME/KEY: exon
<222> LOCATION: (1037)..(1175)
<220> FEATURE:
<221> NAME/KEY: CDS
<222> LOCATION: (1037)..(1172)

<400> SEQUENCE: 7
gctgctcctg ctcgcttcct gccctgca atg gcg gct ctc ctc ctc ctc tcc        52
                                Met Ala Ala Leu Leu Leu Leu Ser
                                 1               5 tcc gcc gct cgg gtacgtagcc ggtaacacat gactcagtca atcttggcac          104
Ser Ala Ala Arg
         10 ttgcggagtt gcggtagctt cagttcttga tttgctgctg cag gtt ggc gtg gct     159
                                                Val Gly Val Ala
                                                             15 gcg cca ctg gcg ctg agg cag cag cgc ccg gtg gtg ctg ccc ggt ggc     207
Ala Pro Leu Ala Leu Arg Gln Gln Arg Pro Val Val Leu Pro Gly Gly
         20                  25                  30 cag ctc cgc acg gga agc ggc gcc ggc gca gcg tcg gcg tgg gcg gcg     255
Gln Leu Arg Thr Gly Ser Gly Ala Gly Ala Ala Ser Ala Trp Ala Ala
     35                  40                  45 cgc cct ctc cgg ccg gag ctc gcc gcg gtc tcc cgc ccc gcc gtc ccc     303
Arg Pro Leu Arg Pro Glu Leu Ala Ala Val Ser Arg Pro Ala Val Pro
 50                  55                  60 gcc cgc ggc agg gcg cct ctg ttc cgg cct cgc gca t gtaacgcctc        350
Ala Arg Gly Arg Ala Pro Leu Phe Arg Pro Arg Ala
65                  70                  75 tgcggcccca ttcaattcta gctctaccac aactgattgg tgtaggactg actgacgaat   410
ttcgccatgg atttggttgt gaggagcag gg atg gcg tcg tct cag att gcc      462
                                   Trp Met Ala Ser Ser Gln Ile Ala
                                                             80 agc tcc gcc ttc acc tgg ggc acc atc gcc gtc ctc cct ttc tac act     510
Ser Ser Ala Phe Thr Trp Gly Thr Ile Ala Val Leu Pro Phe Tyr Thr
 85                  90                  95                 100 ctc atg gtc gtc gcc ccc aac gcc gac gtc gtaagaattc ctcaatcctc       560
Leu Met Val Val Ala Pro Asn Ala Asp Val
                105                 110 caacccacac acacacaatc gaattgctct cacttgctcc tctaatcttt ctctgtgctg   620
```

```
gcgcag acc aag cgt gcc gtg gat agc agc gcg ccg tac gtc gcc ctc        668
       Thr Lys Arg Ala Val Asp Ser Ser Ala Pro Tyr Val Ala Leu
                115                 120 ggc atc ctc tac gcc tac ctg ctc tac cta tcc tgg act ccc gac acc      716
Gly Ile Leu Tyr Ala Tyr Leu Leu Tyr Leu Ser Trp Thr Pro Asp Thr
125             130                 135                 140 cta cgc gcc atg ttc gcc agc aag tac tgg ctc ccc gag gtcagtcaat       765
Leu Arg Ala Met Phe Ala Ser Lys Tyr Trp Leu Pro Glu
                145                 150 caatcagtga caccactctg cactccatga tcactagcat tctctcaacc tttctcttct    825 cctgcgcag ttg acg ggg atc gtc agg atg ttc gcc agc gag atg acc gtc    876
          Leu Thr Gly Ile Val Arg Met Phe Ala Ser Glu Met Thr Val
                  155                 160                 165 gcc tcc gcc tgg atc cac ctc cta gcc gtc gac ctc ttc gcc gca ag       923
Ala Ser Ala Trp Ile His Leu Leu Ala Val Asp Leu Phe Ala Ala Arg
        170                 175                 180 gtgagcaaat tcttgattca tgtgtgtagt agtgtaccta tggatgatgg ttgtatgtgt    983
tgcaagcgtg aggaggttgt taaaatggct tgagttttgg gatcacaatg cag g cag    1040
                                                              Gln gtg tac cat gac ggc atc aag aac aac ata gag acc agg cat tcg gtt     1088
Val Tyr His Asp Gly Ile Lys Asn Asn Ile Glu Thr Arg His Ser Val
185             190                 195                 200 tct ctg tgc ctg ctc ttc tgc cca att ggg atc gcg act cac gtt ctg     1136
Ser Leu Cys Leu Leu Phe Cys Pro Ile Gly Ile Ala Thr His Val Leu
        205                 210                 215 act aag gta ctg gcg ggt tca att ggt cgc tca cat tga tcgattgtat      1185
Thr Lys Val Leu Ala Gly Ser Ile Gly Arg Ser His
        220                 225 gtaggttcat attgcttag                                                 1204

<210> SEQ ID NO 8
<211> LENGTH: 228
<212> TYPE: PRT
<213> ORGANISM: Oryza sp.

<400> SEQUENCE: 8

Met Ala Ala Leu Leu Leu Ser Ser Ala Ala Arg Val Gly Val Ala
1               5                   10                  15

Ala Pro Leu Ala Leu Arg Gln Gln Arg Pro Val Val Leu Pro Gly Gly
            20                  25                  30

Gln Leu Arg Thr Gly Ser Gly Ala Gly Ala Ala Ser Ala Trp Ala Ala
        35                  40                  45

Arg Pro Leu Arg Pro Glu Leu Ala Ala Val Ser Arg Pro Ala Val Pro
    50                  55                  60

Ala Arg Gly Arg Ala Pro Leu Phe Arg Pro Arg Ala Trp Met Ala Ser
65                  70                  75                  80

Ser Gln Ile Ala Ser Ser Ala Phe Thr Trp Gly Thr Ile Ala Val Leu
                85                  90                  95

Pro Phe Tyr Thr Leu Met Val Val Ala Pro Asn Ala Asp Val Thr Lys
            100                 105                 110

Arg Ala Val Asp Ser Ser Ala Pro Tyr Val Ala Leu Gly Ile Leu Tyr
        115                 120                 125

Ala Tyr Leu Leu Tyr Leu Ser Trp Thr Pro Asp Thr Leu Arg Ala Met
    130                 135                 140

Phe Ala Ser Lys Tyr Trp Leu Pro Glu Leu Thr Gly Ile Val Arg Met
145                 150                 155                 160
```

```
Phe Ala Ser Glu Met Thr Val Ala Ser Ala Trp Ile His Leu Leu Ala
                165                 170                 175

Val Asp Leu Phe Ala Ala Arg Gln Val Tyr His Asp Gly Ile Lys Asn
            180                 185                 190

Asn Ile Glu Thr Arg His Ser Val Ser Leu Cys Leu Leu Phe Cys Pro
        195                 200                 205

Ile Gly Ile Ala Thr His Val Leu Thr Lys Val Leu Ala Gly Ser Ile
    210                 215                 220

Gly Arg Ser His
225

<210> SEQ ID NO 9
<211> LENGTH: 684
<212> TYPE: DNA
<213> ORGANISM: Triticum sp.
<220> FEATURE:
<221> NAME/KEY: CDS
<222> LOCATION: (1)..(684)

<400> SEQUENCE: 9
```

| | | | | | | | | | | | | | | | | |
|---|---|---|---|---|---|---|---|---|---|---|---|---|---|---|---|---|
| atg | gcg | gcc | tcc | tcc | ccc | tcc | gcc | ctc | gcg | ctc | tcc | ccc | tcc | acg | cgg | 48 |
| Met | Ala | Ala | Ser | Ser | Pro | Ser | Ala | Leu | Ala | Leu | Ser | Pro | Ser | Thr | Arg | |
| 1 | | | | 5 | | | | | 10 | | | | | 15 | | |
| gtg | gta | gct | ggt | ccg | tcc | ctg | ctg | ctt | gct | gtg | aag | cgg | acg | ccg | gcg | 96 |
| Val | Val | Ala | Gly | Pro | Ser | Leu | Leu | Leu | Ala | Val | Lys | Arg | Thr | Pro | Ala | |
| | | | 20 | | | | | 25 | | | | | 30 | | | |
| acg | cga | gtg | gcc | gcc | gct | ccc | tcc | ggc | cag | ctc | ccc | gcc | tgc | tct | tgg | 144 |
| Thr | Arg | Val | Ala | Ala | Ala | Pro | Ser | Gly | Gln | Leu | Pro | Ala | Cys | Ser | Trp | |
| | | 35 | | | | | 40 | | | | | 45 | | | | |
| ggc | cct | ctc | cgg | ccg | gag | ctc | gcc | ccg | gcc | cct | ggc | ccc | tgc | gcc | gcc | 192 |
| Gly | Pro | Leu | Arg | Pro | Glu | Leu | Ala | Pro | Ala | Pro | Gly | Pro | Cys | Ala | Ala | |
| 50 | | | | | 55 | | | | | 60 | | | | | | |
| cgc | tgc | agg | gcg | cct | ctg | ctc | cgg | cct | cgc | gca | tgg | atg | tcc | acg | tcc | 240 |
| Arg | Cys | Arg | Ala | Pro | Leu | Leu | Arg | Pro | Arg | Ala | Trp | Met | Ser | Thr | Ser | |
| 65 | | | | | 70 | | | | | 75 | | | | | 80 | |
| cag | att | gcc | agc | tcc | gcc | ttc | aca | ctg | ggc | acc | gtc | gcc | gtc | ctc | ccc | 288 |
| Gln | Ile | Ala | Ser | Ser | Ala | Phe | Thr | Leu | Gly | Thr | Val | Ala | Val | Leu | Pro | |
| | | | | 85 | | | | | 90 | | | | | 95 | | |
| ttc | tac | acg | ctc | atg | atc | gcc | gcc | ccc | aac | gcc | agc | atc | act | aag | cgc | 336 |
| Phe | Tyr | Thr | Leu | Met | Ile | Ala | Ala | Pro | Asn | Ala | Ser | Ile | Thr | Lys | Arg | |
| | | | | 100 | | | | | 105 | | | | | 110 | | |
| acc | gtg | gag | agc | acc | gcc | ccc | tac | gtg | gcg | ctc | ggc | ctc | ctc | tac | gcc | 384 |
| Thr | Val | Glu | Ser | Thr | Ala | Pro | Tyr | Val | Ala | Leu | Gly | Leu | Leu | Tyr | Ala | |
| | | | 115 | | | | | 120 | | | | | 125 | | | |
| tac | ctg | ctc | tac | ctc | tcc | tgg | acc | ccc | gac | acc | atc | cgc | gcc | atg | ttc | 432 |
| Tyr | Leu | Leu | Tyr | Leu | Ser | Trp | Thr | Pro | Asp | Thr | Ile | Arg | Ala | Met | Phe | |
| | | 130 | | | | | 135 | | | | | 140 | | | | |
| gcc | agc | aag | tac | tgg | ctc | ccc | gag | ttg | cct | ggc | att | gtg | agg | atg | ttc | 480 |
| Ala | Ser | Lys | Tyr | Trp | Leu | Pro | Glu | Leu | Pro | Gly | Ile | Val | Arg | Met | Phe | |
| 145 | | | | | 150 | | | | | 155 | | | | | 160 | |
| gcg | agc | gag | atg | acc | gtc | gcc | tcc | gcc | tgg | atc | cac | ctc | ctt | gcc | gtc | 528 |
| Ala | Ser | Glu | Met | Thr | Val | Ala | Ser | Ala | Trp | Ile | His | Leu | Leu | Ala | Val | |
| | | | | 165 | | | | | 170 | | | | | 175 | | |
| gac | ctc | ttc | gcc | gca | agg | cag | gtg | tac | caa | gat | gga | atc | aag | aac | aac | 576 |
| Asp | Leu | Phe | Ala | Ala | Arg | Gln | Val | Tyr | Gln | Asp | Gly | Ile | Lys | Asn | Asn | |
| | | | | 180 | | | | | 185 | | | | | 190 | | |
| atc | gag | acc | agg | cat | tcg | gtt | tcg | ctc | tgc | ctg | ctc | ttc | tgc | ccc | atc | 624 |
| Ile | Glu | Thr | Arg | His | Ser | Val | Ser | Leu | Cys | Leu | Leu | Phe | Cys | Pro | Ile | |
| | | | 195 | | | | | 200 | | | | | 205 | | | |
| ggg | atc | gcc | gct | cac | gcg | ctc | act | aag | gta | ctg | gcg | ggt | tcc | aca | ggt | 672 |
| Gly | Ile | Ala | Ala | His | Ala | Leu | Thr | Lys | Val | Leu | Ala | Gly | Ser | Thr | Gly | |

```
                    210                 215                 220 cga ccg cac tga                                                       684
Arg Pro His
225

<210> SEQ ID NO 10
<211> LENGTH: 227
<212> TYPE: PRT
<213> ORGANISM: Triticum sp.

<400> SEQUENCE: 10

Met Ala Ala Ser Ser Pro Ser Ala Leu Ala Leu Ser Pro Ser Thr Arg
1               5                   10                  15

Val Val Ala Gly Pro Ser Leu Leu Ala Val Lys Arg Thr Pro Ala
            20                  25                  30

Thr Arg Val Ala Ala Ala Pro Ser Gly Gln Leu Pro Ala Cys Ser Trp
        35                  40                  45

Gly Pro Leu Arg Pro Glu Leu Ala Pro Ala Pro Gly Pro Cys Ala Ala
    50                  55                  60

Arg Cys Arg Ala Pro Leu Leu Arg Pro Arg Ala Trp Met Ser Thr Ser
65                  70                  75                  80

Gln Ile Ala Ser Ser Ala Phe Thr Leu Gly Thr Val Ala Val Leu Pro
                85                  90                  95

Phe Tyr Thr Leu Met Ile Ala Ala Pro Asn Ala Ser Ile Thr Lys Arg
            100                 105                 110

Thr Val Glu Ser Thr Ala Pro Tyr Val Ala Leu Gly Leu Leu Tyr Ala
        115                 120                 125

Tyr Leu Leu Tyr Leu Ser Trp Thr Pro Asp Thr Ile Arg Ala Met Phe
    130                 135                 140

Ala Ser Lys Tyr Trp Leu Pro Glu Leu Pro Gly Ile Val Arg Met Phe
145                 150                 155                 160

Ala Ser Glu Met Thr Val Ala Ser Ala Trp Ile His Leu Leu Ala Val
                165                 170                 175

Asp Leu Phe Ala Ala Arg Gln Val Tyr Gln Asp Gly Ile Lys Asn Asn
            180                 185                 190

Ile Glu Thr Arg His Ser Val Ser Leu Cys Leu Leu Phe Cys Pro Ile
        195                 200                 205

Gly Ile Ala Ala His Ala Leu Thr Lys Val Leu Ala Gly Ser Thr Gly
    210                 215                 220

Arg Pro His
225

<210> SEQ ID NO 11
<211> LENGTH: 22
<212> TYPE: PRT
<213> ORGANISM: Artificial
<220> FEATURE:
<223> OTHER INFORMATION: consensus
<220> FEATURE:
<221> NAME/KEY: MISC_FEATURE
<222> LOCATION: (3)..(3)
<223> OTHER INFORMATION: Xaa = any non-hydrophilic amino acid,
      preferably Ser ou Cys
<220> FEATURE:
<221> NAME/KEY: MISC_FEATURE
<222> LOCATION: (4)..(4)
<223> OTHER INFORMATION: Xaa = any non-hydrophilic amino acid,
      preferably Val or Ala
<220> FEATURE:
<221> NAME/KEY: MISC_FEATURE
<222> LOCATION: (6)..(6)
<223> OTHER INFORMATION: Xaa = any non-hydrophilic amino acid,
```

```
      preferably Ala or Thr
<220> FEATURE:
<221> NAME/KEY: MISC_FEATURE
<222> LOCATION: (7)..(7)
<223> OTHER INFORMATION: Xaa = any non-hydrophilic amino acid,
      preferably Val, Leu or Trp
<220> FEATURE:
<221> NAME/KEY: MISC_FEATURE
<222> LOCATION: (10)..(10)
<223> OTHER INFORMATION: Xaa = any non-hydrophilic amino acid,
      preferably Thr, Val or Ile
<220> FEATURE:
<221> NAME/KEY: MISC_FEATURE
<222> LOCATION: (20)..(20)
<223> OTHER INFORMATION: Xaa = any non-hydrophilic amino acid,
      preferably Val or Ile
<220> FEATURE:
<221> NAME/KEY: MISC_FEATURE
<222> LOCATION: (21)..(21)
<223> OTHER INFORMATION: Xaa = any non-hydrophilic amino acid,
      preferably Val or Ala

<400> SEQUENCE: 11

Ala Ser Xaa Xaa Phe Xaa Xaa Gly Thr Xaa Ala Val Leu Pro Phe Tyr
1               5                   10                  15

Thr Leu Met Xaa Xaa Ala
            20

<210> SEQ ID NO 12
<211> LENGTH: 19
<212> TYPE: PRT
<213> ORGANISM: Artificial
<220> FEATURE:
<223> OTHER INFORMATION: consensus
<220> FEATURE:
<221> NAME/KEY: MISC_FEATURE
<222> LOCATION: (1)..(1)
<223> OTHER INFORMATION: Xaa=any non-hydrophilic amino acid, preferably
      Ser, Gly or Thr
<220> FEATURE:
<221> NAME/KEY: MISC_FEATURE
<222> LOCATION: (2)..(2)
<223> OTHER INFORMATION: Xaa=any non-hydrophilic amino acid, preferably
      Val or Ala
<220> FEATURE:
<221> NAME/KEY: MISC_FEATURE
<222> LOCATION: (5)..(5)
<223> OTHER INFORMATION: Xaa=any non-hydrophilic amino acid, preferably
      Val or Ile
<220> FEATURE:
<221> NAME/KEY: MISC_FEATURE
<222> LOCATION: (6)..(6)
<223> OTHER INFORMATION: Xaa=any non-hydrophilic amino acid, preferably
      Ile or Ala
<220> FEATURE:
<221> NAME/KEY: MISC_FEATURE
<222> LOCATION: (9)..(9)
<223> OTHER INFORMATION: Xaa=any non-hydrophilic amino acid, preferably
      Val, Leu or  Ile
<220> FEATURE:
<221> NAME/KEY: MISC_FEATURE
<222> LOCATION: (12)..(12)
<223> OTHER INFORMATION: Xaa=any non-hydrophilic amino acid, preferably
      Val or  Ala
<220> FEATURE:
<221> NAME/KEY: MISC_FEATURE
<222> LOCATION: (17)..(17)
<223> OTHER INFORMATION: Xaa=any non-hydrophilic amino acid, preferably
      Ile or Leu

<400> SEQUENCE: 12

Xaa Xaa Pro Tyr Xaa Xaa Leu Gly Xaa Leu Tyr Xaa Tyr Leu Leu Tyr
1               5                   10                  15

Xaa Ser Trp
```

```
<210> SEQ ID NO 13
<211> LENGTH: 18
<212> TYPE: PRT
<213> ORGANISM: Artificial
<220> FEATURE:
<223> OTHER INFORMATION: consensus
<220> FEATURE:
<221> NAME/KEY: MISC_FEATURE
<222> LOCATION: (3)..(3)
<223> OTHER INFORMATION: Xaa = any non-hydrophilic amino acid,
      preferably Leu or Val
<220> FEATURE:
<221> NAME/KEY: MISC_FEATURE
<222> LOCATION: (12)..(12)
<223> OTHER INFORMATION: Xaa = any non-hydrophilic amino acid,
      preferably Val or Ala

<400> SEQUENCE: 13

Met Thr Xaa Ala Ser Ala Trp Ile His Leu Leu Xaa Val Asp Leu Phe
1               5                   10                  15

Ala Ala

<210> SEQ ID NO 14
<211> LENGTH: 17
<212> TYPE: PRT
<213> ORGANISM: Artificial
<220> FEATURE:
<223> OTHER INFORMATION: consensus
<220> FEATURE:
<221> NAME/KEY: MISC_FEATURE
<222> LOCATION: (11)..(11)
<223> OTHER INFORMATION: Xaa = any non-hydrophilic amino acid,
      preferably Val or Ile
<220> FEATURE:
<221> NAME/KEY: MISC_FEATURE
<222> LOCATION: (14)..(14)
<223> OTHER INFORMATION: Xaa = any non-hydrophilic amino acid,
      preferably Val, Leu or Ala
<220> FEATURE:
<221> NAME/KEY: MISC_FEATURE
<222> LOCATION: (15)..(15)
<223> OTHER INFORMATION: Xaa = any non-hydrophilic amino acid,
      preferably Ala,Thr or Ser
<220> FEATURE:
<221> NAME/KEY: MISC_FEATURE
<222> LOCATION: (17)..(17)
<223> OTHER INFORMATION: Xaa = any non-hydrophilic amino acid,
      preferably Val,  Ala or Phe

<400> SEQUENCE: 14

Ser Val Ser Leu Cys Leu Leu Phe Cys Pro Xaa Gly Ile Xaa Xaa His
1               5                   10                  15

Xaa

<210> SEQ ID NO 15
<211> LENGTH: 5
<212> TYPE: PRT
<213> ORGANISM: Artificial
<220> FEATURE:
<223> OTHER INFORMATION: consensus
<220> FEATURE:
<221> NAME/KEY: MISC_FEATURE
<222> LOCATION: (4)..(4)
<223> OTHER INFORMATION: Xaa = Met or Trp

<400> SEQUENCE: 15

Ser Lys Tyr Xaa Leu
1               5

<210> SEQ ID NO 16
<211> LENGTH: 137
```

```
<212> TYPE: PRT
<213> ORGANISM: Artificial
<220> FEATURE:
<223> OTHER INFORMATION: consensus
<220> FEATURE:
<221> NAME/KEY: MISC_FEATURE
<222> LOCATION: (5)..(5)
<223> OTHER INFORMATION: Xaa = any non-hydrophilic amino acid,
      preferably Ser or Cys
<220> FEATURE:
<221> NAME/KEY: MISC_FEATURE
<222> LOCATION: (6)..(6)
<223> OTHER INFORMATION: Xaa = any non-hydrophilic amino acid,
      preferably Val or Ala
<220> FEATURE:
<221> NAME/KEY: MISC_FEATURE
<222> LOCATION: (8)..(8)
<223> OTHER INFORMATION: Xaa = any non-hydrophilic amino acid,
      preferably Ala or Thr
<220> FEATURE:
<221> NAME/KEY: MISC_FEATURE
<222> LOCATION: (9)..(9)
<223> OTHER INFORMATION: Xaa = any non-hydrophilic amino acid,
      preferably Val, Leu or Trp
<220> FEATURE:
<221> NAME/KEY: MISC_FEATURE
<222> LOCATION: (12)..(12)
<223> OTHER INFORMATION: Xaa = any non-hydrophilic amino acid,
      preferably Thr, Val or Ile
<220> FEATURE:
<221> NAME/KEY: MISC_FEATURE
<222> LOCATION: (22)..(22)
<223> OTHER INFORMATION: Xaa = any non-hydrophilic amino acid,
      preferably Val or Ile
<220> FEATURE:
<221> NAME/KEY: MISC_FEATURE
<222> LOCATION: (23)..(23)
<223> OTHER INFORMATION: Xaa = any non-hydrophilic amino acid,
      preferably Val or Ala
<220> FEATURE:
<221> NAME/KEY: MISC_FEATURE
<222> LOCATION: (26)..(26)
<223> OTHER INFORMATION: Xaa =  Lys or Asn
<220> FEATURE:
<221> NAME/KEY: MISC_FEATURE
<222> LOCATION: (28)..(28)
<223> OTHER INFORMATION: Xaa = Glu, Asp or Ser
<220> FEATURE:
<221> NAME/KEY: MISC_FEATURE
<222> LOCATION: (29)..(29)
<223> OTHER INFORMATION: Xaa = any non-hydrophilic amino acid,
      preferably Val or Ile
<220> FEATURE:
<221> NAME/KEY: MISC_FEATURE
<222> LOCATION: (32)..(32)
<223> OTHER INFORMATION: Xaa = Arg or Lys
<220> FEATURE:
<221> NAME/KEY: MISC_FEATURE
<222> LOCATION: (33)..(33)
<223> OTHER INFORMATION: Xaa = any non-hydrophilic amino acid,
      preferably Cys, Thr or Ala
<220> FEATURE:
<221> NAME/KEY: MISC_FEATURE
<222> LOCATION: (34)..(34)
<223> OTHER INFORMATION: Xaa = any non-hydrophilic amino acid,
      preferably Met or Val
<220> FEATURE:
<221> NAME/KEY: MISC_FEATURE
<222> LOCATION: (35)..(35)
<223> OTHER INFORMATION: Xaa = Glu or Asp
<220> FEATURE:
<221> NAME/KEY: MISC_FEATURE
<222> LOCATION: (37)..(37)
<223> OTHER INFORMATION: Xaa = any non-hydrophilic amino acid,
      preferably Ser, Gly or Thr
<220> FEATURE:
<221> NAME/KEY: MISC_FEATURE
<222> LOCATION: (38)..(38)
<223> OTHER INFORMATION: Xaa = any non-hydrophilic amino acid,
      preferably Val or Ala
```

```
<220> FEATURE:
<221> NAME/KEY: MISC_FEATURE
<222> LOCATION: (41)..(41)
<223> OTHER INFORMATION: Xaa = any non-hydrophilic amino acid,
      preferably Val or Ile
<220> FEATURE:
<221> NAME/KEY: MISC_FEATURE
<222> LOCATION: (42)..(42)
<223> OTHER INFORMATION: Xaa = any non-hydrophilic amino acid,
      preferably Ile or Ala
<220> FEATURE:
<221> NAME/KEY: MISC_FEATURE
<222> LOCATION: (45)..(45)
<223> OTHER INFORMATION: Xaa = any non-hydrophilic amino acid,
      preferably Val, Leu or Ile
<220> FEATURE:
<221> NAME/KEY: MISC_FEATURE
<222> LOCATION: (48)..(48)
<223> OTHER INFORMATION: Xaa = any non-hydrophilic amino acid,
      preferably Val or Ala
<220> FEATURE:
<221> NAME/KEY: MISC_FEATURE
<222> LOCATION: (53)..(53)
<223> OTHER INFORMATION: Xaa = any non-hydrophilic amino acid,
      preferably Ile or Leu
<220> FEATURE:
<221> NAME/KEY: MISC_FEATURE
<222> LOCATION: (58)..(58)
<223> OTHER INFORMATION: Xaa = Glu or Asp
<220> FEATURE:
<221> NAME/KEY: MISC_FEATURE
<222> LOCATION: (60)..(60)
<223> OTHER INFORMATION: Xaa = any non-hydrophilic amino acid,
      preferably Ile or Leu
<220> FEATURE:
<221> NAME/KEY: MISC_FEATURE
<222> LOCATION: (61)..(61)
<223> OTHER INFORMATION: Xaa = any non-hydrophilic amino acid,
      preferably Arg or Lys
<220> FEATURE:
<221> NAME/KEY: MISC_FEATURE
<222> LOCATION: (62)..(62)
<223> OTHER INFORMATION: Xaa = any non-hydrophilic amino acid,
      preferably Ala or Tyr
<220> FEATURE:
<221> NAME/KEY: MISC_FEATURE
<222> LOCATION: (65)..(65)
<223> OTHER INFORMATION: Xaa = any non-hydrophilic amino acid,
      preferably Ala or Ser
<220> FEATURE:
<221> NAME/KEY: MISC_FEATURE
<222> LOCATION: (69)..(69)
<223> OTHER INFORMATION: Xaa = any non-hydrophilic amino acid,
      preferably Met or Trp
<220> FEATURE:
<221> NAME/KEY: MISC_FEATURE
<222> LOCATION: (74)..(74)
<223> OTHER INFORMATION: Xaa = any non-hydrophilic amino acid,
      preferably Ser, Pro, Ala or Thr
<220> FEATURE:
<221> NAME/KEY: MISC_FEATURE
<222> LOCATION: (77)..(77)
<223> OTHER INFORMATION: Xaa = any non-hydrophilic amino acid,
      preferably Val or Ala
<220> FEATURE:
<221> NAME/KEY: MISC_FEATURE
<222> LOCATION: (78)..(78)
<223> OTHER INFORMATION: Xaa =  Arg or Lys
<220> FEATURE:
<221> NAME/KEY: MISC_FEATURE
<222> LOCATION: (81)..(81)
<223> OTHER INFORMATION: Xaa = any non-hydrophilic amino acid,
      preferably Ala or Ser
<220> FEATURE:
<221> NAME/KEY: MISC_FEATURE
<222> LOCATION: (86)..(86)
<223> OTHER INFORMATION: Xaa = any non-hydrophilic amino acid,
      preferably Leu or Val
<220> FEATURE:
<221> NAME/KEY: MISC_FEATURE
```

```
<222> LOCATION: (95)..(95)
<223> OTHER INFORMATION: Xaa = any non-hydrophilic amino acid,
      preferably Val or Ala
<220> FEATURE:
<221> NAME/KEY: MISC_FEATURE
<222> LOCATION: (106)..(106)
<223> OTHER INFORMATION: Xaa = His, Asn or Gln
<220> FEATURE:
<221> NAME/KEY: MISC_FEATURE
<222> LOCATION: (109)..(109)
<223> OTHER INFORMATION: Xaa = any non-hydrophilic amino acid,
      preferably Ile or Leu
<220> FEATURE:
<221> NAME/KEY: MISC_FEATURE
<222> LOCATION: (110)..(110)
<223> OTHER INFORMATION: Xaa = Lys, Arg or Glu
<220> FEATURE:
<221> NAME/KEY: MISC_FEATURE
<222> LOCATION: (112)..(112)
<223> OTHER INFORMATION: Xaa = Gln or Asn
<220> FEATURE:
<221> NAME/KEY: MISC_FEATURE
<222> LOCATION: (113)..(113)
<223> OTHER INFORMATION: Xaa = any non-hydrophilic amino acid,
      preferably Val or Ile
<220> FEATURE:
<221> NAME/KEY: MISC_FEATURE
<222> LOCATION: (128)..(128)
<223> OTHER INFORMATION: Xaa = any non-hydrophilic amino acid,
      preferably Val or Ile
<220> FEATURE:
<221> NAME/KEY: MISC_FEATURE
<222> LOCATION: (131)..(131)
<223> OTHER INFORMATION: Xaa = any non-hydrophilic amino acid,
      preferably Val, Leu or Ala
<220> FEATURE:
<221> NAME/KEY: MISC_FEATURE
<222> LOCATION: (132)..(132)
<223> OTHER INFORMATION: Xaa = any non-hydrophilic amino acid,
      preferably Ala, Thr or Ser
<220> FEATURE:
<221> NAME/KEY: MISC_FEATURE
<222> LOCATION: (134)..(134)
<223> OTHER INFORMATION: Xaa = any non-hydrophilic amino acid,
      preferably Val, Ala or Phe
<220> FEATURE:
<221> NAME/KEY: MISC_FEATURE
<222> LOCATION: (135)..(135)
<223> OTHER INFORMATION: Xaa = any non-hydrophilic amino acid,
      preferably Leu or Val

<400> SEQUENCE: 16

Gln Ile Ala Ser Xaa Xaa Phe Xaa Xaa Gly Thr Xaa Ala Val Leu Pro
1               5                   10                  15

Phe Tyr Thr Leu Met Xaa Xaa Ala Pro Xaa Ala Xaa Xaa Thr Lys Xaa
            20                  25                  30

Xaa Xaa Xaa Ser Xaa Xaa Pro Tyr Xaa Xaa Leu Gly Xaa Leu Tyr Xaa
        35                  40                  45

Tyr Leu Leu Tyr Xaa Ser Trp Thr Pro Xaa Thr Xaa Xaa Xaa Met Phe
    50                  55                  60

Xaa Ser Lys Tyr Xaa Leu Pro Glu Leu Xaa Gly Ile Xaa Xaa Met Phe
65                  70                  75                  80

Xaa Ser Glu Met Thr Xaa Ala Ser Ala Trp Ile His Leu Leu Xaa Val
                85                  90                  95

Asp Leu Phe Ala Ala Arg Gln Val Tyr Xaa Asp Gly Xaa Xaa Asn Xaa
            100                 105                 110

Xaa Glu Thr Arg His Ser Val Ser Leu Cys Leu Leu Phe Cys Pro Xaa
        115                 120                 125

Gly Ile Xaa Xaa His Xaa Xaa Thr Lys
    130                 135
```

<210> SEQ ID NO 17
<211> LENGTH: 68
<212> TYPE: PRT
<213> ORGANISM: Arabidopsis thaliana

<400> SEQUENCE: 17

```
Met Gly Phe Ser Ser Phe Ile Ser Gln Pro Leu Ser Ser Ser Leu Ser
1               5                   10                  15

Val Met Lys Arg Asn Val Ser Ala Lys Arg Ser Glu Leu Cys Leu Asp
            20                  25                  30

Ser Ser Lys Ile Arg Leu Asp His Arg Trp Ser Phe Ile Gly Gly Ser
        35                  40                  45

Arg Ile Ser Val Gln Ser Asn Ser Tyr Thr Val Val His Lys Lys Phe
    50                  55                  60

Ser Gly Val Arg
65
```

<210> SEQ ID NO 18
<211> LENGTH: 82
<212> TYPE: PRT
<213> ORGANISM: Zea mays

<400> SEQUENCE: 18

```
Met Ala Pro Cys Ala Ser Pro Ser Ala Leu Ala Leu Ser Ala Ser Thr
1               5                   10                  15

Arg Val Ser Ser Phe Pro Leu Thr Leu Arg Pro Arg Pro Arg Pro Glu
            20                  25                  30

Ala Arg Val Pro Arg Ala Pro Gly Gly Ala Gln Leu Arg Pro Ala Thr
        35                  40                  45

Ala Cys Ser Trp Pro Arg Pro Leu Leu Pro Glu Leu Ala Pro Ala Phe
    50                  55                  60

Pro Arg Ala Gly Ala Arg Ser Ala Gly Arg Pro Gln Pro Leu Phe Arg
65                  70                  75                  80

Pro Arg
```

<210> SEQ ID NO 19
<211> LENGTH: 79
<212> TYPE: PRT
<213> ORGANISM: Zea mays

<400> SEQUENCE: 19

```
Met Ala Pro Cys Ala Ser Pro Ser Ala Leu Ala Leu Ser Ala Ser Thr
1               5                   10                  15

Arg Val Ser Ile Leu Arg Leu Pro Leu Ala Leu Arg Gln Arg Ala Glu
            20                  25                  30

Ala Arg Val Pro Gly Ala Gln Phe Arg Pro Ser Thr Ala Cys Ser Trp
        35                  40                  45

Ala Arg Pro Leu Leu Pro Glu Leu Ala Gly Ala Val Pro Arg Ala Gly
    50                  55                  60

Ala Arg Gly Thr Gly Arg Arg Thr Gln Pro Leu Phe Arg Pro Arg
65                  70                  75
```

<210> SEQ ID NO 20
<211> LENGTH: 75
<212> TYPE: PRT
<213> ORGANISM: Oryza sativa

<400> SEQUENCE: 20

```
Met Ala Ala Leu Leu Leu Leu Ser Ser Ala Ala Arg Val Gly Val Ala
```

```
                1               5                  10                 15
Ala Pro Leu Ala Leu Arg Gln Gln Arg Pro Val Val Leu Pro Gly Gly
                    20                  25                  30

Gln Leu Arg Thr Gly Ser Gly Ala Gly Ala Ala Ser Ala Trp Ala Ala
            35                  40                  45

Arg Pro Leu Arg Pro Glu Leu Ala Ala Val Ser Arg Pro Ala Val Pro
        50                  55                  60

Ala Arg Gly Arg Ala Pro Leu Phe Arg Pro Arg
65                  70                  75

<210> SEQ ID NO 21
<211> LENGTH: 74
<212> TYPE: PRT
<213> ORGANISM: Triticum aestivum

<400> SEQUENCE: 21

Met Ala Ala Ser Ser Pro Ser Ala Leu Ala Leu Ser Pro Ser Thr Arg
1               5                  10                  15

Val Val Ala Gly Pro Ser Leu Leu Leu Ala Val Lys Arg Thr Pro Ala
                    20                  25                  30

Thr Arg Val Ala Ala Ala Pro Ser Gly Gln Leu Pro Ala Cys Ser Trp
            35                  40                  45

Gly Pro Leu Arg Pro Glu Leu Ala Pro Ala Pro Gly Pro Cys Ala Ala
        50                  55                  60

Arg Cys Arg Ala Pro Leu Leu Arg Pro Arg
65                  70

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
ggttttaccc ttctatactc                                             20

<210> SEQ ID NO 23
<211> LENGTH: 19
<212> TYPE: DNA
<213> ORGANISM: Artificial
<220> FEATURE:
<223> OTHER INFORMATION: primer

<400> SEQUENCE: 23
cattttagct attccagac                                              19

<210> SEQ ID NO 24
<211> LENGTH: 25
<212> TYPE: DNA
<213> ORGANISM: Artificial
<220> FEATURE:
<223> OTHER INFORMATION: primer

<400> SEQUENCE: 24
atgccccagg acatcgtgat ttcat                                       25

<210> SEQ ID NO 25
<211> LENGTH: 24
<212> TYPE: DNA
<213> ORGANISM: Artificial
<220> FEATURE:
<223> OTHER INFORMATION: primer
```

```
<400> SEQUENCE: 25
ttggcggcac ccttagctgg atca                                          24

<210> SEQ ID NO 26
<211> LENGTH: 24
<212> TYPE: DNA
<213> ORGANISM: Artificial
<220> FEATURE:
<223> OTHER INFORMATION: primer

<400> SEQUENCE: 26
aatgactctt gcttctgctt ggat                                          24

<210> SEQ ID NO 27
<211> LENGTH: 26
<212> TYPE: DNA
<213> ORGANISM: Artificial
<220> FEATURE:
<223> OTHER INFORMATION: primer

<400> SEQUENCE: 27
gctttggtta cgaaatgcga aacgat                                        26

<210> SEQ ID NO 28
<211> LENGTH: 23
<212> TYPE: DNA
<213> ORGANISM: Artificial
<220> FEATURE:
<223> OTHER INFORMATION: primer

<400> SEQUENCE: 28
cttcttgctt tcacccttgg tgt                                           23

<210> SEQ ID NO 29
<211> LENGTH: 22
<212> TYPE: DNA
<213> ORGANISM: Artificial
<220> FEATURE:
<223> OTHER INFORMATION: primer

<400> SEQUENCE: 29
tgtcagggtt gtatccgacc tt                                            22

<210> SEQ ID NO 30
<211> LENGTH: 31
<212> TYPE: DNA
<213> ORGANISM: Artificial
<220> FEATURE:
<223> OTHER INFORMATION: primer

<400> SEQUENCE: 30
aaaaaagcag gctatttgaa tcagagatgg g                                  31

<210> SEQ ID NO 31
<211> LENGTH: 32
<212> TYPE: DNA
<213> ORGANISM: Artificial
<220> FEATURE:
<223> OTHER INFORMATION: primer

<400> SEQUENCE: 31
aagaaagctg ggtcaggagg ttttcaagtt gc                                 32

<210> SEQ ID NO 32
<211> LENGTH: 29
```

<212> TYPE: DNA
<213> ORGANISM: Artificial
<220> FEATURE:
<223> OTHER INFORMATION: primer

<400> SEQUENCE: 32
ggggacaagt ttgtacaaaa aagcaggct                29

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33
ggggaccact ttgtacaaga aagctgggt                29

<210> SEQ ID NO 34
<211> LENGTH: 731
<212> TYPE: DNA
<213> ORGANISM: Artificial
<220> FEATURE:
<223> OTHER INFORMATION: Synthetic sequence

<400> SEQUENCE: 34
ggtaccatgg cccatgcgc cagcccaagc gccctggccc tgagcgccag caccgcgtg      60 tccagcttcc cgctgaccct gaggccaagg ccaaggcctg aggcagggt gccaagggcc    120 ccaggcggcg ctcagctgag gccagccacc gcctgctctt ggccgaggcc gctgctgcca   180
gagctggccc cagccttccc aagggctggc gctcgcagcg ccggcaggcc acagccactg   240
ttccgcccga gggccatgat gaccacctcc cagatcgcca gctgcgcctt cactgtgggc   300
accgtggccg tgctgccgtt ctacaccctg atggtggtgg ccccgaacgc cgacatcacc   360
aagcgcaccg tggagagcag cgccccatac gtggccctgg gcctgctgta cgcctacctg   420
ctgtacctga gctggacccc ggacaccctg agggccatgt tcgccagcaa gtactggctg   480
cccgagctgc caggcatcgt gcgcatgttc gcctccgaga tgaccgtggc cagcgcctgg   540
atccacctgc tggccgtgga cctgttcgcc gccaggcagg tgtaccacga cggcctgaag   600
aacaacatcg agacccgcca cagcgtgtcc ctgtgcctgc tcttctgccc agtgggcatc   660
ctggcccacg tggtgaccaa ggtgctggct ggcgccgctg gcaggtccca ctgatgagcg   720
gccgcgagct c                                                       731

<210> SEQ ID NO 35
<211> LENGTH: 20
<212> TYPE: DNA
<213> ORGANISM: Zea mays

<400> SEQUENCE: 35
ggcgatttta ttcaccactg                          20

<210> SEQ ID NO 36
<211> LENGTH: 20
<212> TYPE: DNA
<213> ORGANISM: Zea mays

<400> SEQUENCE: 36
gaccatgagc gtgtagaagg                          20

<210> SEQ ID NO 37
<211> LENGTH: 20

```
<212> TYPE: DNA
<213> ORGANISM: Zea mays

<400> SEQUENCE: 37
ggcgagaatt cgccactacc                                              20

<210> SEQ ID NO 38
<211> LENGTH: 20
<212> TYPE: DNA
<213> ORGANISM: Zea mays

<400> SEQUENCE: 38
gaccatgagg gtgtagaagg                                              20
```

1

PLANTS WITH INCREASED TOLERANCE TO WATER DEFICIT

CROSS REFERENCE TO RELATED APPLICATIONS

This application is a national stage application filed under 35 U.S.C. 371 of International Application No. PCT/IB2007/002785, filed Jun. 18, 2007, which claims priority from European Patent Application No. 06290983.3, filed Jun. 16, 2006.

FIELD AND BACKGROUND OF THE INVENTION

The present invention relates to the identification of proteins useful for improving tolerance to water deficit in plants, to nucleic acid sequences encoding said proteins, and to their use for increasing the tolerance of plants to water deficit.

"Water deficit" relates to a situation where a plant has insufficient water for optimal functioning of its physiological processes.

Water deficit is one of the most important abiotic stresses affecting plants, and is one of the main factors responsible for yield loss in crops. Water deficit can severely affect plant yield, growth and reproduction. Therefore, it is important to identify genes that have the capacity to improve plant tolerance to water deficit.

The plant hormone abscisic acid (ABA) is renowned for being a stress hormone. Its levels rise in response to abiotic stress, in particular upon water deficit, and it has been shown to be necessary for the induction of a variety of adaptive responses from stomatal closure to osmotic adjustment (NAMBARA and MARION-POLL, Annu Rev Plant Biol, 56, 165-85, 2005).

ABA is a sesquiterpenoid ($C_{15}$) that is synthesized in plants via an indirect pathway using carotenoid precursors. In plants carotenoids are essential components of the photosynthetic apparatus and are the red, orange and yellow pigments found in many flowers and fruit. Early ABA biosynthesis reactions occur, therefore, in plastids. The direct precursors of ABA are the xanthophylls zeaxanthin, violaxanthin and neoxanthin with the first ABA biosynthesis specific reaction being the oxidative cleavage of 9-cis-epoxycarotenoids (FIG. 1). The cleavage product xanthoxin is then transited to the cytoplasm where it undergoes conversion to abscisic aldehyde followed by oxidation to yield ABA. The biosynthetic pathway of ABA is schematized on FIG. 1.

Genes encoding the enzymes for most of the steps of the ABA biosynthesis pathway have been cloned or their function confirmed using ABA-deficient mutants. The zeaxanthin epoxidase (ZEP) gene was first cloned from a *Nicotiana plumbaginifolia* insertion mutant and is defective in the *Arabidopsis* aba1 mutant (MARIN et al., Embo J, 15, 2331-42, 1996). The ZEP enzyme catalyses the conversion of zeaxanthin to violaxanthin via antheraxanthin in two successive epoxidation reactions (FIG. 1). The maize VP14 mutant is mutated in a 9-cis-epoxycarotenoid dioxygenase (NCED) gene required for oxidative cleavage (SCHWARTZ et al., Science, 276, 1872-4, 1997; TAN et al., Proc Natl Acad Sci USA, 94, 12235-40, 1997) and in vitro activity assays suggested that either violaxanthin or neoxanthin cis-isomers could be substrates. A short chain dehydrogenase/reductase (SDR) catalyses the oxidation of xanthoxin to abscisic aldehyde (FIG. 1) and was identified using *Arabidopsis* aba2 mutants (CHENG et al., Plant Cell, 14, 2723-43, 2002; GONZALEZ-GUZMAN et al., Plant Cell, 14, 1833-46, 2002). Defects in two genes affect the last step of ABA biosynthesis (FIG. 1) one encoding the abscisic aldehyde oxidase apoprotein and the second an enzyme required for the sulfuration of the molybdenum cofactor. The aba3 mutant was shown to have a lesion in a gene encoding a molybdenum cofactor sulfurase (SCHWARTZ et al., Plant Physiol, 114, 161-6, 1997), and the corresponding gene was identified by positional cloning (BITTNER et al., J. Biol. Chem. 276, 40381-4, 2001; XIONG et al., Plant Cell 13, 2063-83, 2001), whereas the role of an aldehyde oxidase in the last step of ABA biosynthesis was confirmed, thanks to the *Arabidopsis* aldehyde oxidase3 (aao3) mutant (SEO et al., Proc Natl Acad Sci USA, 97, 12908-13, 2000).

Most of the *Arabidopsis* ABA-deficient mutants identified to date have been demonstrated to present germination that is resistant to paclobutrazol, or equivalent gibberellic acid (GA) biosynthesis inhibitors. This phenotype is related to the antagonistic effects of ABA and GA on germination making the balance between the levels of the two hormones determinant as to whether a seed germinates or not. In an ABA-deficient mutant the GA requirement for germination is thus less than in a wild-type seed and paclobutrazol has been used effectively as a screening method to identify mutants affected in ABA biosynthesis or signalling (JACOBSEN and OLSZEWSKI, Plant Cell, 5, 887-96, 1993; LEON-KLOOSTERZIEL et al., Plant J, 10, 655-61, 1996; NAMBARA et al., Plant Cell Physiol, 39, 853-8, 1998). In accordance with the role of ABA in responses to water deficit, ABA-deficient mutants also often show phenotypes related to defects in stomatal closure; increased water loss and a wilty phenotype on water deficit (SEO et al., Proc Natl Acad Sci USA, 97, 12908-13, 2000; KOORNNEEF et al., Theor. Appl. Genet. 61, 385-93, 1982; LEON-KLOOSTERZIEL et al., Plant Physiol, 110, 233-40, 1996). It has been shown that overexpression of *Arabidopsis* NCED genes, AtNCED3 and AtNCED6, increases endogenous ABA levels, and improves tolerance to water deficit (IUCHI et al., Plant J, 27, 325-33, 2001; LEFEBVRE et al., Plant J, 45, 309-319, 2006).

SUMMARY OF THE INVENTION

The inventors have now identified in *Arabidopsis thaliana* a protein involved in the conversion of violaxanthin to neoxanthin, which is hereinafter referred to as ABA4. Mutants of the ABA4 gene wherein the ABA4 protein is no longer functional are affected in ABA biosynthesis and in response to water deficit.

The inventors have further found orthologs of ABA4 from *Arabidopsis thaliana* in other plants such as maize, wheat and rice.

The nucleotide sequence of an ABA4 gene of *Arabidopsis thaliana* (AtABA4) is available under accession number At1g67080 in the TAIR *Arabidopsis* database. It is reproduced herein as SEQ ID NO: 1, and the corresponding polypeptide sequence is indicated as SEQ ID NO: 2.

Nucleotide sequences of two ABA4 genes from maize (ZmABA4a and ZmABA4b) are indicated herein respectively as SEQ ID NO: 3 (ZmABA4a) and SEQ ID NO: 5 (ZmABA4b), and the corresponding polypeptide sequences are respectively indicated as SEQ ID NO: 4 (ZmABA4a) and SEQ ID NO: 6 (ZmABA4b).

The nucleotide sequence of an ABA4 gene from rice (OsABA4) is indicated herein as SEQ ID NO: 7 and the corresponding polypeptide sequence is indicated as SEQ ID NO: 8.

The nucleotide sequence encoding an ABA4 protein from wheat (TaABA4) is indicated herein as SEQ ID NO: 9 and the corresponding polypeptide sequence is indicated as SEQ ID NO: 10.

AtABA4 from *Arabidopsis thaliana* is predicted to be 220 amino acids in length with the first 68 amino acids presenting the features of a chloroplast signal peptide as predicted by the Chloro P programme (EMANELSSON et al., Protein Sci. 8, 978-84, 1999); rich in hydroxylated amino acids, few acidic amino acids and an alanine residue at position 69 in agreement with the chloroplast transit peptide cleavage-site motif (KEEGSTRA et al., Annu. Rev. Plant Physiol. Mol. Biol. 40, 471-501, 1989; GAVEL and von HEIJNE, FEBS Lett. 261, 455-458, 1990). The mature ABA4 protein has a predicted molecular mass of 17.0 kDa and a theoretical pI of 7.91.

ZmABA4a from maize is predicted to be 235 amino acids in length with the first 82 amino acids presenting the features of a chloroplast signal peptide as predicted by the Chloro P programme (cited above). This maize mature ABA4 protein has a predicted molecular mass of 16.7 kDa and a theoretical pI of 8.53.

ZmABA4b from maize is predicted to be 232 amino acids in length with the first 79 amino acids presenting the features of a chloroplast signal peptide as predicted by the Chloro P programme. This mature ZmABA4b protein has a predicted molecular mass of 16.7 kDa and a theoretical pI of 8.54.

OsABA4 from rice is predicted to be 228 amino acids in length with the first 75 amino acids presenting the features of a chloroplast signal peptide as predicted by the Chloro P programme. This mature OsABA4 protein has a predicted molecular mass of 16-2 kDa and a theoretical pI of 8.03.

TaABA4 from wheat is predicted to be 227 amino acids in length with the first 74 amino acids presenting the features of a chloroplast signal peptide as predicted by the Chloro P programme. This mature TaABA4b protein has a predicted molecular mass of 16.8 kDa and a theoretical pI of 9.01.

Hydropathy analyses of the ABA4 proteins of *Arabidopsis*, maize, rice and wheat indicate the presence of 4 helical transmembrane domains, but no domains of known function were identified.

The present invention provides a method for increasing the tolerance of a plant to water deficit, wherein said method comprises overexpressing in said plant an ABA4 polypeptide comprising the following regions:

a) a chloroplast signal peptide;

b) a region comprising a sequence having at least 60%, and preferably at least 65%, and by order of increasing preference, at least 70%, 75%, 80%, 85%, 90%, 95%, 98%, or 99% identity with the region 69-220 of the polypeptide SEQ ID NO: 2, or with the region 83-235 of the polypeptide SEQ ID NO: 4, or with the region 80-232 of the polypeptide SEQ ID NO: 6 or with the region 76-228 of the polypeptide SEQ ID NO: 8, with the region 75-227 of the polypeptide SEQ ID NO: 10.

Unless otherwise specified, the sequence identity values provided herein are calculated using the algorithm of NEEDLEMAN and WUNSCH (J Mol Biol. 48, 443-53, 1970) under default parameters.

According to a preferred embodiment of the invention, region b) of said polypeptide comprises:

i) four domains defined by the following sequences (one letter code):

```
                                        (SEQ ID NO: 11)
htm 1:  ASX₁X₂FX₃X₄gtX₅AVLPFYTLMX₆X₂A, (SEQ ID NO: 12)
htm 2:  X₇X₂PYX₆X₈LGX₉LYX₂YLLYx₁₀SW, (SEQ ID NO: 13)
htm 3:  MTX₁₁ASAWIHLLX₂VDLFAA, (SEQ ID NO: 14)
htm 4:  SVSLCLLFCPX₆GIX₁₂X₁₃HX₁₄,
``` wherein $X_1$ to $X_{14}$ represent a non-hydrophilic amino acid (i.e any amino acid except R, K, N, Q, or E), and preferably, $X_1$=S or C, $X_2$=V or A, $X_3$=A or T, $X_4$=V, L or W, $X_5$=T, V or I, $X_6$=V or I, $X_7$=S, G or T, $X_8$=I or A, $X_9$=V, L or I, $X_{10}$=I or L, $X_{11}$=L or V, $X_{12}$=V, L or A, $X_{13}$=A, T, or S, $X_{14}$=V, A or F; these domains represent predicted transmembrane domains;

ii) a block of five amino acids SKYX₁₅L (SEQ ID NO: 15), wherein $X_{15}$=M or W, between domains htm2 and htm3;

iii) a protein kinase C motif (Prosite PDOC00005) defined by the sequence TKX₁₆ wherein $X_{16}$=R or K, between domains htm1 and htm2.

Advantageously, region b) comprises the following sequence:

```
                                        (SEQ ID NO: 16)
QIASX₁X₂FX₃X₄GTX₅AVLPFYTLMX₆X₂APX₁₇AX₁₈X₆TKX₁₆X₁₉

X₂₀X₂₁SX₇X₂PYX₆X₈LGX₉LYX₂YLLYX₁₀SWTPX₂₁TX₁₀X₁₆X₂₂

MFX₂₃SKYX₁₅LPELX₂₄GIX₂X₁₆MFX₂₃SEMTX₁₁ASAWIHLLX₂VD

LFAARQVYX₂₅DGX₁₀X₂₆NX₂₇X₆ETRHSVSLCLLFCPX₆GIX₁₂X₁₃

HX₁₄X₁₁TK
``` wherein $X_1$ to $X_{16}$ are as defined above and $X_{17}$=K or N, $X_{18}$=E, D, or S, $X_{19}$=C, T, or A $X_{20}$=M or V, $X_{21}$ E or D, $X_{22}$=A or Y, $X_{23}$=A or S, $X_{24}$=S, P, A, or T, $X_{25}$=H, N, or Q, $X_{26}$=K, R, or E, $X_{27}$=Q or N.

The chloroplast signal peptide a) can be a signal peptide of an ABA4 polypeptide. For instance, it can be selected among:

a peptide having the following sequence:

```
                                        (SEQ ID NO: 17)
MGFSSFISQPLSSSLSVMKRNVSAKRSELCLDSSKIRLDHRWSFIGGSRI

SVQSNSYTVVHKKFSGVR
``` a peptide having the following sequence:

```
                                        (SEQ ID NO: 18)
MAPCASPSALALSASTRVSSFPLTLRPRPRPEARVPRAPGGAQLRPATAC

SWPRPLLPELAPAFPRAGARSAGRPQPLFRPR
``` a peptide having the following sequence:

```
                                        (SEQ ID NO: 19)
MAPCASPSALALSASTRVSILRLPLALRQRAEARVPGAQFRPSTACSWAR

PLLPELAGAVPRAGARGTGRRTQPLFRPR
``` a peptide having the following sequence:

(SEQ ID NO: 20)
MAALLLLSSAARVGVAAPLALRQQRPVVLPGGQLRTGSGAGAASAWAARP

LRPELAAVSRPAVPARGRAPLFRPR a peptide having the following sequence:

(SEQ ID NO: 21)
MAASSPSALALSPSTRVVAGPSLLLAVKRTPATRVAAAPSGQLPACSWGP

LRPELAPAPGPCAARCRAPLLRPR

The chloroplast signal peptide a) can also be any transit peptide for a polypeptide localized in the chloroplast such as those identified in proteomic analyses (FERRO et al. Mol. Cell. Proteomics 2, 325-345, 2003), or those disclosed in PCT WO2004/001050.

Preferably, said ABA4 polypeptide is selected among AtABA4 (SEQ ID NO: 2), ZmABA4a (SEQ ID NO: 4), ZmABA4b (SEQ ID NO: 6), OsABA4 (SEQ ID NO: 8) and TaABA4 (SEQ ID NO: 10). Other ABA4 polypeptides suitable for carrying out the invention include in particular those encoded by genes that are orthologs of AtABA4, ZmABA4a, ZmABA4b, OsABA4 or TaABA4. They can be identified for instance by screening plant EST databases to select candidate ESTs encoding polypeptides having the above-defined percent of identity with SEQ ID NO: 2, 4, 6, 8 or 10 or by screening libraries of plant cDNAs with degenerate nucleic acid probes which can be derived from any of SEQ ID NO: 2, 4, 6, 8 or 10, or from regions which are conserved between these sequences. The selected ESTs, or the selected cDNAs can then be checked for the presence of the sequences encoding the 4 transmembrane domains and the protein kinase C motif defined above and the conserved sequence SEQ ID NO: 15.

The term "plant" as used herein, include dicotyledons as well as monocotyledons, and in particular those of agronomical interest, as crop plants (for instance rice, maize, wheat, barley, rapeseed, soybean, peas, sunflower, etc. . . . ) as fruit, vegetables or ornamental plants (for instance solanaceaous or rosaceous plant).

"Overexpressing" a polypeptide refers either to artificially expressing said polypeptide in plants which do not naturally express it, or to artificially increasing its expression (for instance by adding at least one additional copy of a sequence encoding said polypeptide) in plants which naturally express it.

The invention also provides means for carrying out said overexpression.

This includes in particular recombinant DNA constructs for expressing an ABA4 polypeptide in a host-cell, or a host organism, in particular a plant cell or a plant. These DNA constructs can be obtained and introduced into said host cell or organism by well-known techniques of recombinant DNA and genetic engineering.

Recombinant DNA constructs of the invention include in particular expression cassettes, comprising a polynucleotide encoding an ABA4 polypeptide as defined above, under the control of an appropriate promoter.

Said promoter can be any promoter functional in a plant cell. The choice of the more appropriate promoter may depend in particular on the chosen host plant, on the organ(s) or tissue(s) targeted for expression, and on the type of expression (i.e. constitutive or inducible) that one wishes to obtain.

A large choice of promoters suitable for expression of heterologous genes in plants is available in the art. They can be obtained for instance from plants, plant viruses, or bacteria such as *Agrobacterium*. They include constitutive promoters, i.e. promoters which are active in most tissues and cells and under most environmental conditions, tissue or cell specific promoters which are active only or mainly in certain tissues or certain cell types, and inducible promoters that are activated by physical or chemical stimuli, such as those resulting from water deficit.

Non-limitative examples of constitutive promoters that are commonly used in plant cells are the cauliflower mosaic virus (CaMV) 35S promoter, the Nos promoter, the rubisco promoter, the Cassava vein Mosaic Virus (CsVMV) promoter, the rice actin promoter, followed by the rice actin intron (RAP-RAI) contained in the plasmid pAct1-F4 (MCELROY et al., Molecular and General Genetics, 231 (1), 150-160, 1991).

Non-limitative examples of organ or tissue specific promoters that can be used in the present invention include for instance High Molecular Weight Glutenin (HMWG) promoter which is kernel specific (THOMAS and FLAVELL, Plant Cell, 2, 1171-80, 1990), or the leaf specific pPEPc promoter (JEANNEAU et al, Biochimie, 84, 1127-1135, 2002).

Inducible promoters that can be used in the present invention include stress responsive promoters which can be induced by drought stress. By way of example, one can mention promoters comprising a dehydration-responsive element (DRE), such as the rd29A promoter (KASUGA et al. Nature Biotech., 17, 287-291, 1999, NARUSAKA et al., Plant J. 34, 137-48, 2003.)

The expression cassette generally also includes a transcriptional terminator, such as the 35S transcriptional terminator. They may also include other regulatory sequences, such as transcription enhancer sequences or introns (for example the FAD2 intron described in WO 2006/003186, or the actin intron (MCELROY et al., 1991 cited above). Among the terminators which can be used in the constructs of the invention, mention may be made in particular of the 3' end of the *Agrobacterium tumefaciens* nopaline synthase gene (DE-PICKER et al., J Mol Appl Genet. 1 (4):361-370, 1982). Mention may also be made of the 35S polyA terminator of the cauliflower mosaic virus (CaMV), described by FRANCK et al. (Cell. 21 (1):285-94, 1980).

The invention also includes recombinant vectors containing an expression cassette comprising a polynucleotide encoding an ABA4 polypeptide as defined above, under transcriptional control of a suitable promoter. Said expression cassette may be a recombinant expression cassette as defined above, or an expression cassette wherein the polynucleotide encoding an ABA4 polypeptide is under control of its endogenous promoter. Classically, said recombinant vectors also include one or more marker genes, which allow for selection of transformed hosts. As non-limitative examples of marker genes, mention may be made of genes which confers resistance to an antibiotic, for example to hygromycin (HERRERA-ESTRELLA et al., EMBO J. 2 (6): 987-995 1983) or resistance to an herbicide such as the sulfonamide asulam (WO 98/49316).

The selection of suitable vectors and the methods for inserting DNA constructs therein are well known to persons of ordinary skill in the art. The choice of the vector depends on the intended host and on the intended method of transformation of said host. A variety of methods for genetic transformation of plant cells or plants are available in the art for many plant species, dicotyledons or monocotyledons. By way of non-limitative examples, one can mention virus mediated transformation, transformation by microinjection, by electroporation, microprojectile mediated transformation, *Agrobacterium* mediated transformation, and the like.

For instance, in the case of monocotyledons, one can advantageously use the method described by ISHIDA et al. (Nature Biotech. 14, 745-750, 1996).

The invention also provides a host cell comprising a recombinant DNA construct of the invention. Said host cell can be a prokaryotic cell, for instance an *Agrobacterium* cell, or a eukaryotic cell, for instance a plant cell genetically transformed by a DNA construct of the invention.

The invention also comprises plants genetically transformed by a DNA construct of the invention expressing an ABA4 polypeptide. Preferably, said plants are transgenic plants, wherein said construct is contained in a transgene integrated in the plant genome, so that it is passed onto successive plant generations.

The invention also provides a method for producing a transgenic plant having an increased tolerance to water deficit, when compared to a non-transgenic plant, said method comprising the steps consisting of:
transforming at least one plant cell with a vector containing an expression cassette expressing an ABA4 polypeptide, as defined above;
cultivating said transformed plant cell in order to regenerate a plant having in its genome a transgene containing said expression cassette.

The transgenic plants of the present invention includes not only those obtainable by the above-mentioned method, but also the descendents thereof (including hybrid transgenic plants, obtained by crossing at least one transgenic plant of the invention with another plant devoid of the transgene), provided that they comprise in their genome one or more copies of a transgene containing an expression cassette expressing an ABA4 polypeptide.

The expression of the ABA4 polypeptide in said transgenic plants provides them with an increased tolerance to water deficit, when compared to a plant devoid of said transgene.

The invention also encompasses isolated organs or tissues (such as fruits, seeds, leafs, pollen, flowers, roots, tubers) of transgenic plants of the invention.

The invention also provides a method for obtaining plants that have an increased tolerance to water deficit, due to a mutation in the ABA4 gene.

Such a mutation can be localized in the coding regions of the gene or in its cis regulatory regions. It can be a mutation resulting in an increased level of expression of the ABA4 mRNA, and/or of the ABA4 polypeptide, or in a higher stability of said mRNA or polypeptide, or in an increased activity of the ABA4 polypeptide.

The method of the invention includes inducing random mutations in a plant of interest, for instance through EMS mutagenesis, selecting the mutants which have a mutation in the ABA4 gene, and selecting among them those that have an increased tolerance to water deficit, resulting from said mutation.

Selection of mutants which have a mutation in the ABA4 gene can easily be done using methods of high throughput mutagenesis and screening, such as TILLING (Targeting Induced Local Lesions IN Genomes, described by McCALLUM et al, Plant Physiol., 123, 439-442, 2000).

The mutants that have an increased tolerance to water deficit can be identified with various morphological, physiological and/or biochemical assays. By way of example, one can measure water loss rates under conditions of water deficit (for instance through the visualization of leaf temperature by thermal images as described in the examples below), and select the mutants which have a lower water loss rate than the wild type plants. Tolerance to water deficit can also be evaluated by observation of phenotypic characteristics of the plants, such as growth (for instance length and width of the leaves and/or final height of the plant), or yield (number, filling or weight of a predefined number of grains) under conditions of water deficit compared with normal conditions.

The invention also provides means for identifying and selecting plants which are tolerant to water deficit.

The invention thus provides:
a method for identifying an allele of an ABA4 gene associated with a given phenotype of tolerance to water deficit, wherein said method comprises isolating a nucleic acid fragment comprising said ABA4 gene or a portion thereof from at least one plant expressing said phenotype, and sequencing said fragment.

The invention further provides:
a method for identifying polymorphisms associated with tolerance to water deficit, in an ABA4 gene, wherein said method comprises identifying, as described above, at least two different alleles of said ABA4 gene associated with different phenotypes of tolerance to water deficit, and comparing the sequences of said alleles.

Once a polymorphism has been identified, reagents and kits allowing the routine detection of said polymorphism can be designed. Commonly used reagents are nucleic acid probes, or restriction enzymes, or PCR primers, or combinations thereof. The choice of a reagent or of a combination of reagents depends of the nature of the polymorphism.

Preferred kits and reagents are those comprising a set of primers allowing specific PCR amplification of a DNA segment spanning the polymorphic locus. For microsatellites and insertion/deletion polymorphisms, PCR primers may be sufficient, since the allelic forms of the polymorphism may be differentiated by the size of the amplification product. In the case of single nucleotide polymorphisms (SNP), one will generally also use a restriction enzyme, which allows the differentiation of allelic forms by the presence or size of restriction fragments.

The invention also provides a method for testing a plant for its tolerance to water deficit, wherein said method comprises detecting whether an allele of an ABA4 gene associated with a given phenotype of tolerance to water deficit is present in said plant.

For this purpose, it is also possible to use a nucleic acid encoding an ABA4 polypeptide, or a fragment thereof, as a probe or a target for amplification, for selecting plants naturally overexpressing an ABA4 and therefore exhibiting better tolerance to water deficit. Preferably, the amplified fragment has a length of about 500 pb, more preferably, of about 500 to 1000 pb.

By way of example, one can use the following pair of primers: GGCGATTTTATTCACCACTG (SEQ ID NO: 35) and GACCATGAGCGTGTAGAAGG (SEQ ID NO: 36) to amplify a fragment from ZmABA4a, and the following pair of primers: GGCGAGAATTCGCCACTACC (SEQ ID NO:37) and GACCATGAGGGTGTAGAAGG (SEQ ID NO:38) to amplify a fragment from ZmABA4b.

BRIEF DESCRIPTION OF THE DRAWINGS

Foregoing and other objects and advantages of the invention will become more apparent from the following detailed description and accompanying drawings. It is to be understood however that this foregoing detailed description is exemplary only and does not restrict the invention.

(A) Schematic representation of ABA4 gene structure and the sites of the aba4 mutant insertions. Rectangles represent the positions of open reading frames (B) Effect of aba4 mutations on ABA4 gene expression. (C) Alignment of the ABA4 predicted amino acid sequences from *Arabidopsis thaliana* (SEQ ID NO:2), Maize ABA4 proteins: sequences ZmABA4a (SEQ ID NO:4) and ZmABA4b (SEQ ID NO:6), Wheat (SEQ ID NO:10), Rice (SEQ ID NO:8) protein corresponding to annotated gene Os01g03750. Completely conserved residues across 3 or more sequences are shaded black and similar residues conserved across three or more sequences are shaded grey. The arrow indicates the ABA4 putative transit peptide cleavage site, * indicates the site of putative protein kinase C phosphorylation and the lines indicate the position of predicted helical transmembrane (htm) domains identified using PHDhtm (ROST et al., Protein Science 7, 1704-1718, 1996). (D) Analysis and comparison of the hydrophobicity profile of the predicted ABA4 mature protein and freshwater eel rhodopsin (Q90215).

Figure 4:
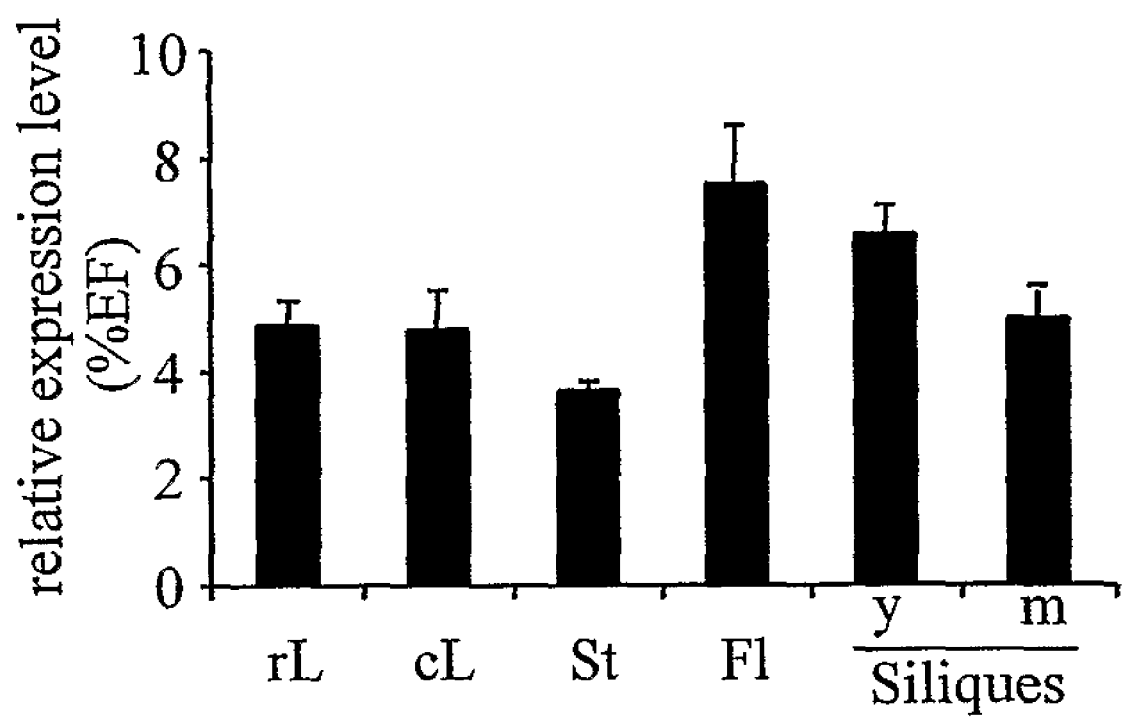

FIG. 4: Tissue specific expression patterns of the ABA4 gene.
(A) Quantitative RT-PCR analysis of ABA4 gene expression in rL, rosette leaves, cL, cauline leaves; St, inflorescence stem; Fl; flowers; y, young siliques, m, mature siliques. Steady state mRNA levels are presented as a percentage of the constitutive EF1αA4 abundance. Error bars represent S.E. values (n=4).

Figure 5:
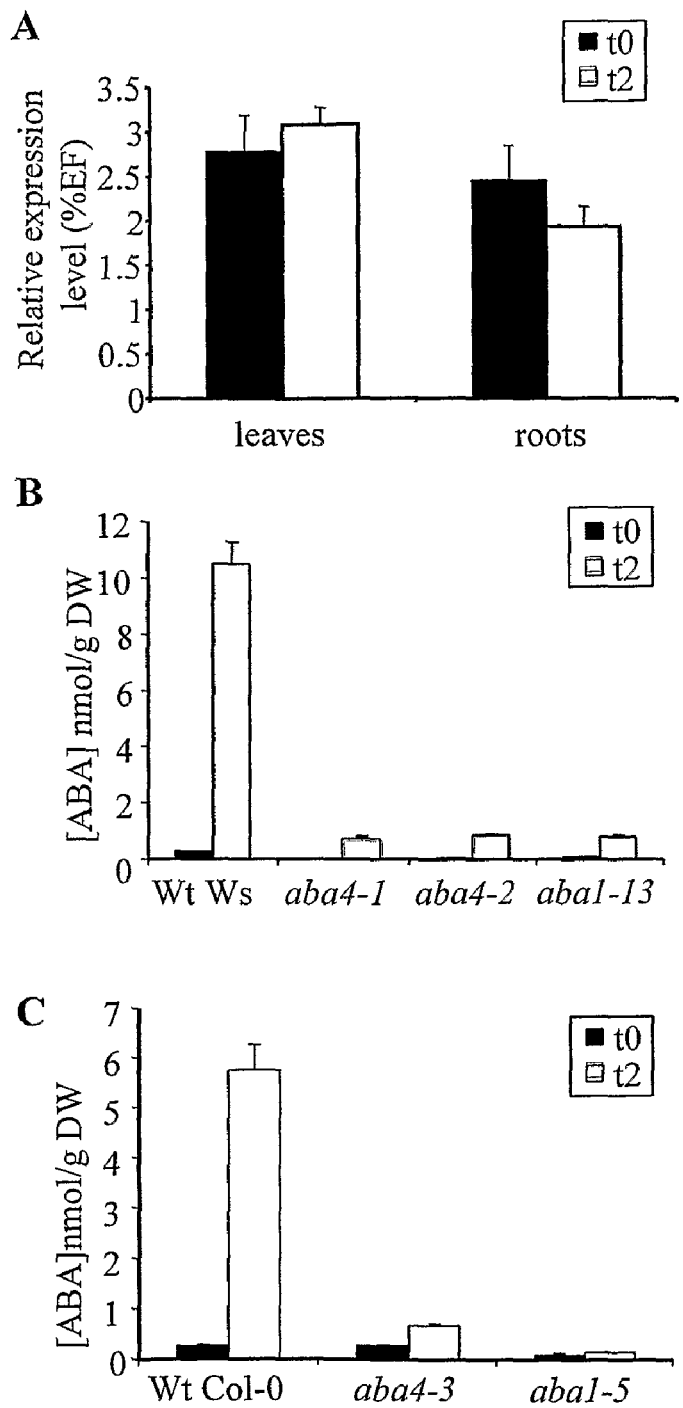

FIG. 5: Effect of dehydration on leaf ABA contents and ABA4 steady state transcript levels.
(A) Quantitative RT-PCR analysis of ABA4 gene expression in leaves and roots of wild-type with (t2) or without a 2 hours dehydration stress (t0). Steady state mRNA levels are presented as a percentage of the constitutive EF1αA4 abundance. Error bars represent S.E. values (n=4). (B, C) ABA levels accumulated in rosettes of 4 week-old plants in response to dehydration for wild-type (Wt) and aba4-1, aba4-2, aba4-3, aba1-5 and aba1-13 mutants from either Ws-2 (B) or Col-0 (C) accessions. ABA content was determined before (t0) and after dehydration for 2 hours (t2). Error bars represent S.E. values (n=≧6).

Figure 6:
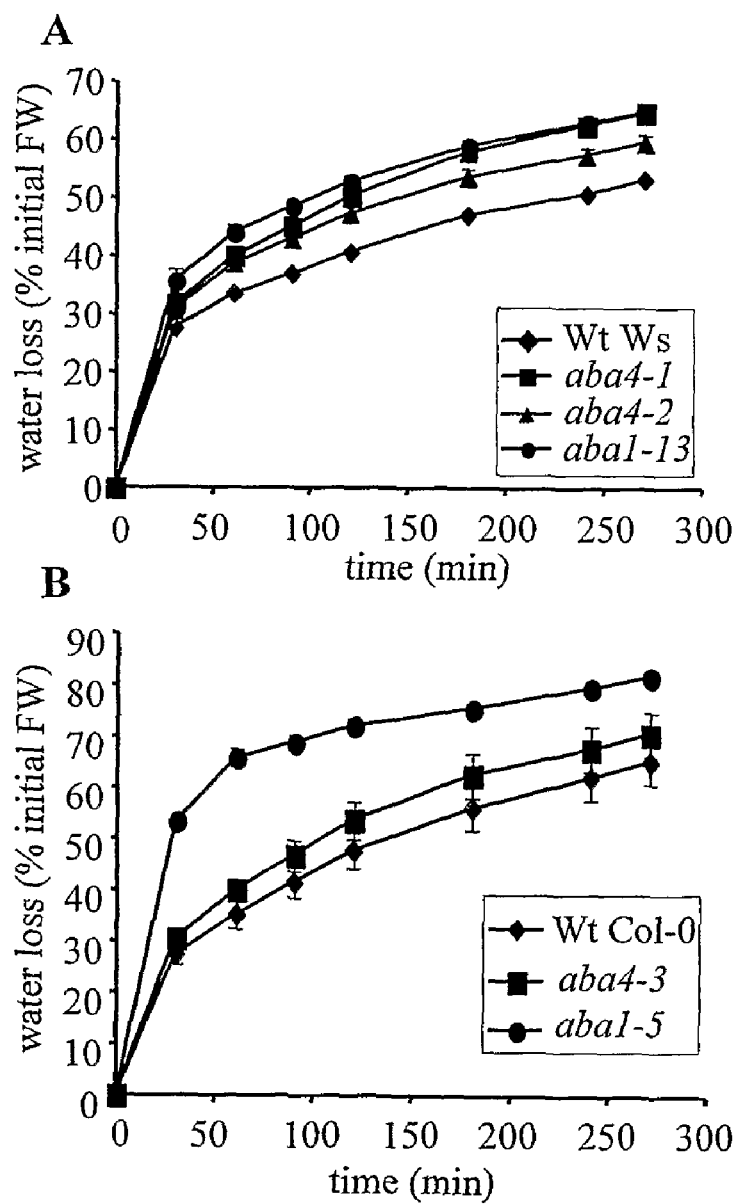

FIG. 6: Phenotype of aba4 mutants on water deficit as compared to aba1 mutant alleles and wild-type.
(A, B) Rapid dehydration phenotypes of aba4-1, aba4-2, aba4-3, aba1-5, aba1-13 mutants and wild-type (Wt). The rate of water loss was determined for mutant and wild-type rosettes from either (A) Ws-2 or (B) Col-0 accessions. Error bars represent S.E. values (n=4).

Figure 7:
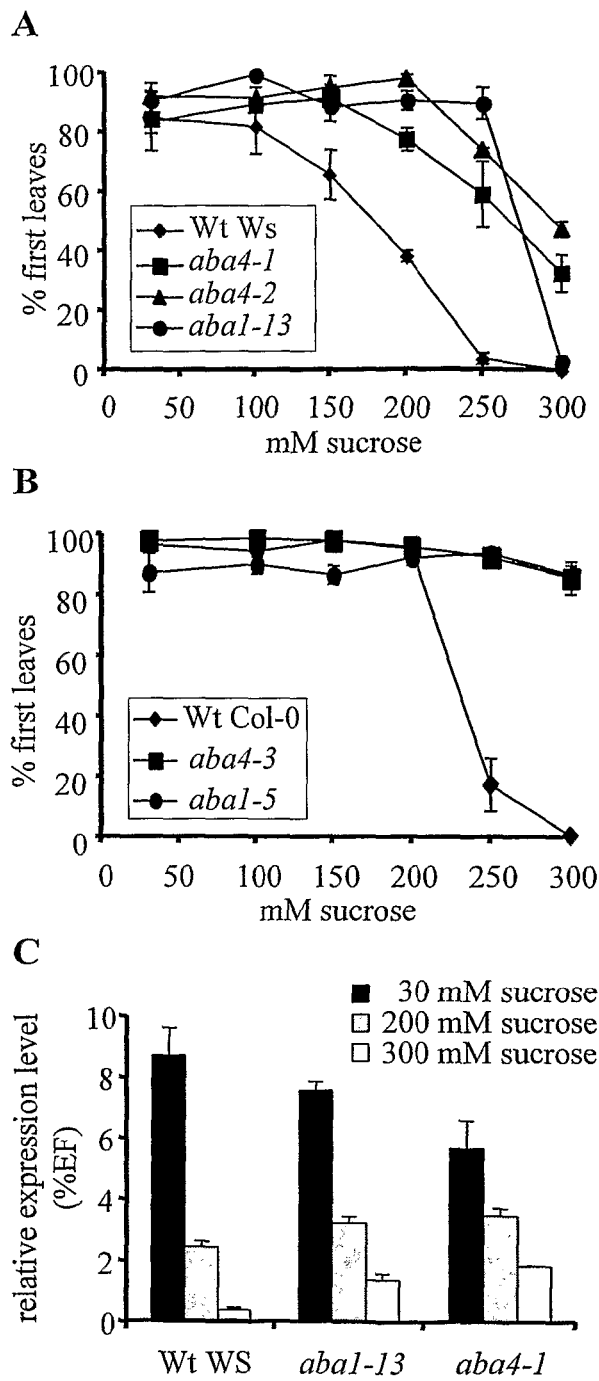

FIG. 7: Role and regulation of ABA4 in the post-germination developmental arrest of seedling growth in response to high sucrose concentrations.
(A, B) Seedlings were grown on media containing increasing concentrations of sucrose for 3 weeks. The number of seedlings with first leaves was scored and compared to the total number of seeds sown for wild-type (Wt) and aba4-1, aba4-2, aba4-3, aba1-5 and aba1-13 mutants from either Ws-2 (A, C) or Col-0 (B, D) accessions. (C) Quantitative RT-PCR analysis of ABA4 gene expression in seedlings of wild-type, aba4-1 or aba1-13 grown for 3 weeks on media containing 30 mM, 200 mM or 300 mM sucrose. Steady state mRNA levels are presented as a percentage of the constitutive EF1αA4 abundance. Error bars represent S.E. values (n=3).

Figure 8:
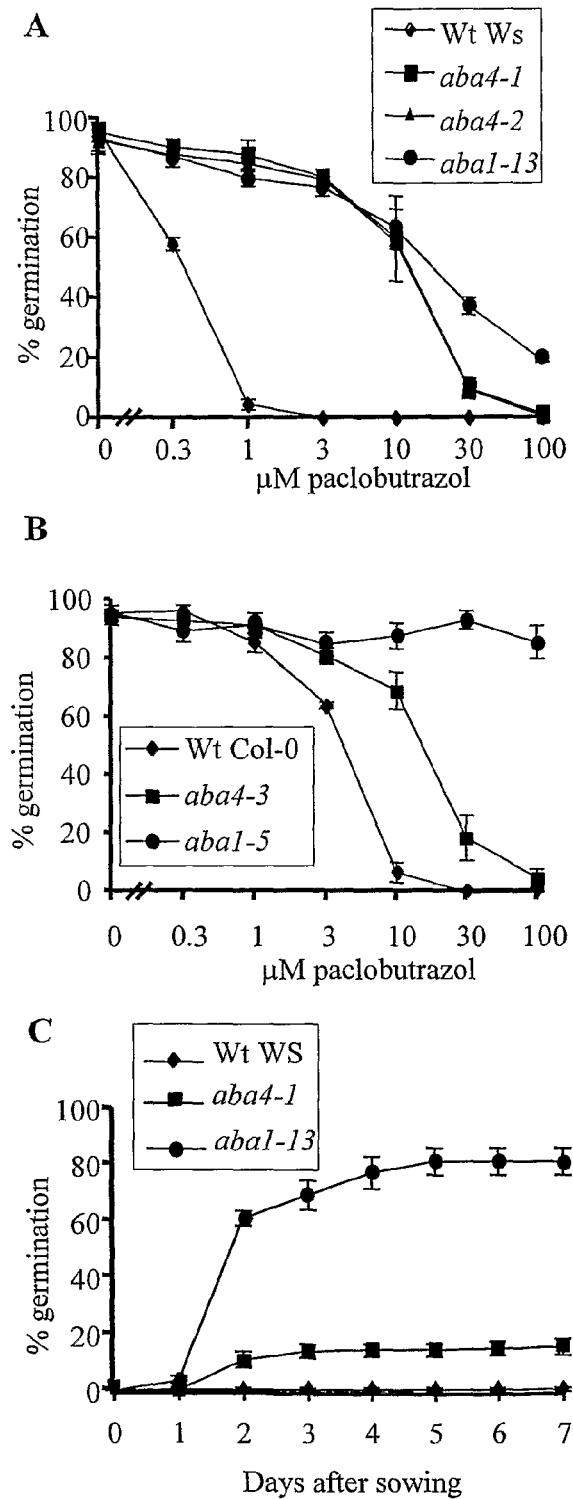

FIG. 8: Seed phenotypes associated with ABA4 deficiency.
(A, B) Paclobutrazol resistance of germinating seeds and (C) germination of freshly harvested seeds. The number of seedlings with green cotyledons (A, B) or seeds with protruding radicle (C) was scored and compared to the total number of seeds sown for wild-type (Wt) and aba4-1, aba4-2, aba4-3, aba1-5 and aba1-13 mutants from either Ws-2 (A, C) or Col-0 (B) accessions. Error bars represent S.E. values (n=3).

Figure 9:
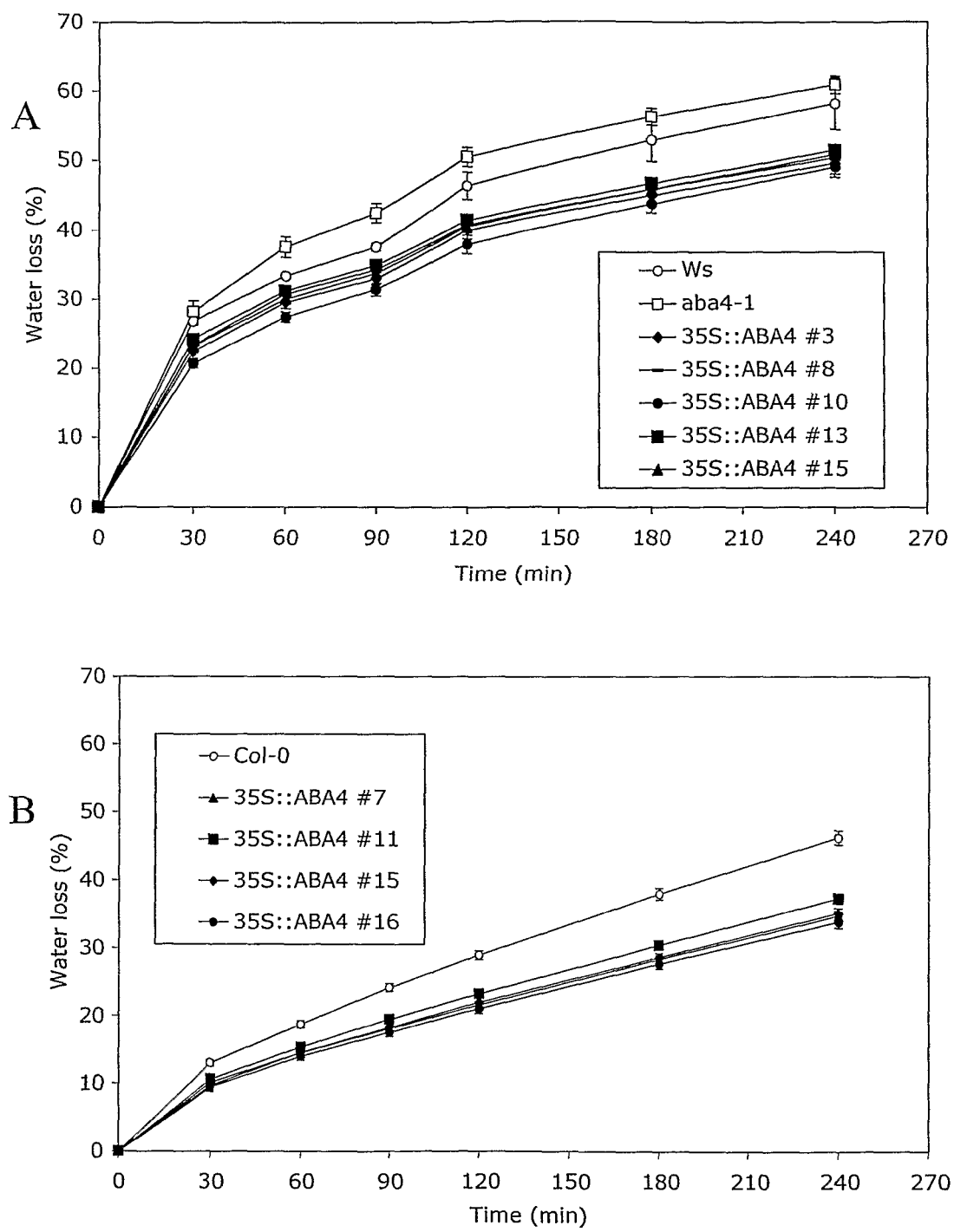

FIG. 9: Effect of water deficit on transgenic plants expressing the ABA4 gene under the control of the 35S promoter. Rapid dehydration of homozogous transgenic plants, selected for hygromycin resistance from the progeny of independent primary transformants in Ws-2 (A) and Col-0 (B) accessions. Error bars represent S.E values (n=4)

Figure 10:
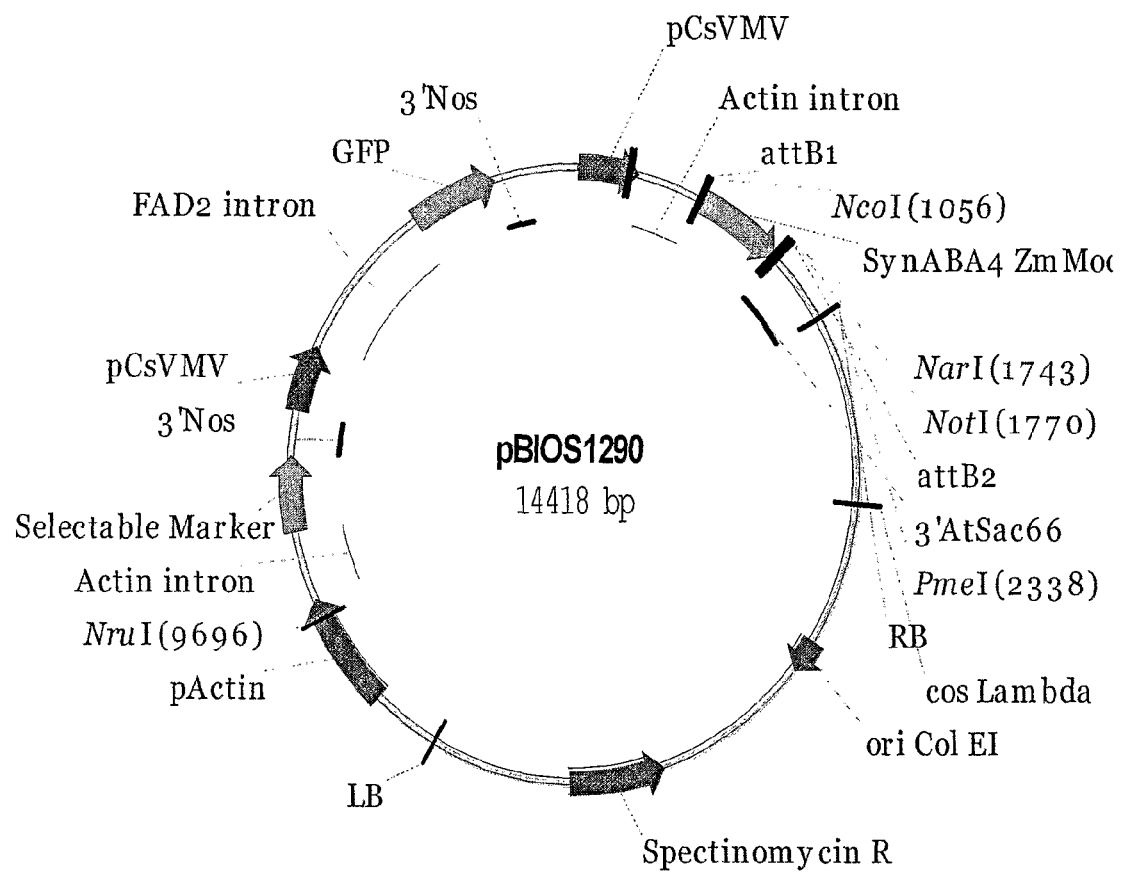

FIG. 10: Schematic representation of the vector pBIOS1290.

Figure 11:
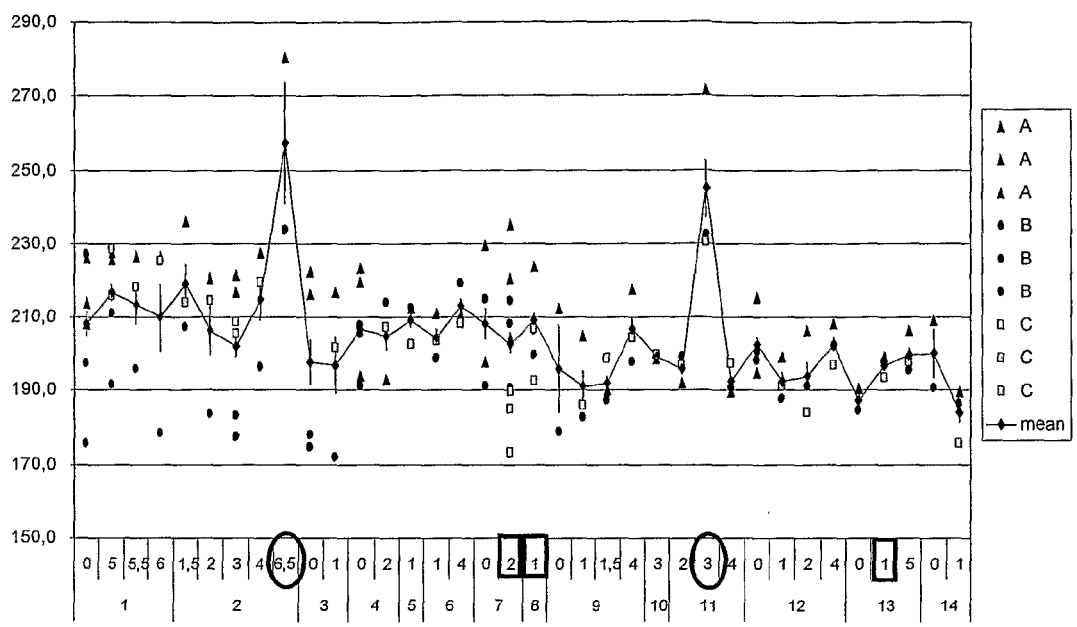
Figure 11:
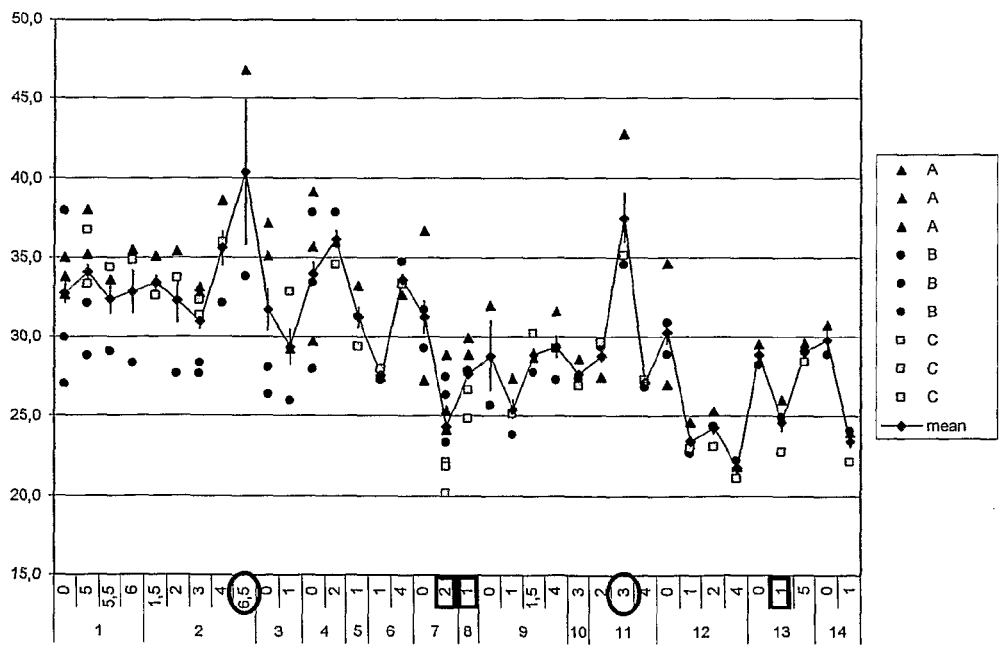

FIG. 11: Carotenoids content of transgenic maize lines overexpressing ABA4.

FIG. 11a represents the total carotenoid content; FIG. 11b represents the t-Violaxanthin content, FIG. 11c represents the c-Neoxanthin content; FIG. 11d represents the c-Violaxanthin content.

HPLC Analysis was performed on 14 transgenic lines (#1-14). For each transgenic line, one to five plants were tested; the number of copies of the construct for each tested plant is indicated above the number of the transgenic line. The graph (-♦-) represents the mean of three independent HPLC measures (A, B and C).

Figure 12:
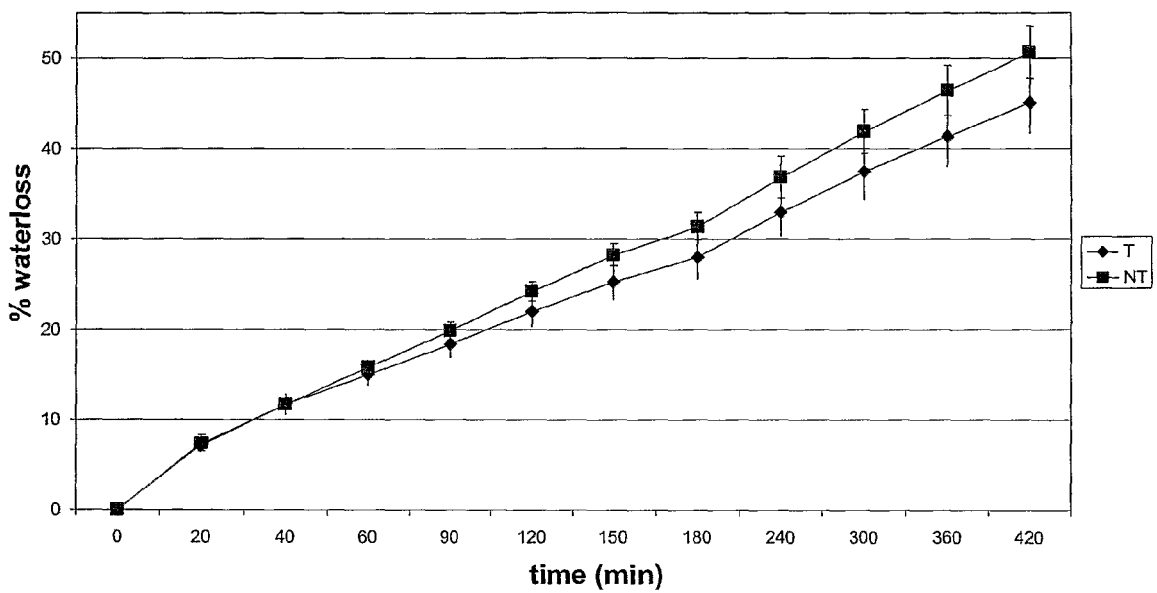

FIG. 12: Loss of water under dessication conditions in transgenic T: -♦-) maize lines overexpressing ABA4 compared to non-transgenic (NT: -■-) plants. Each point represents the mean of three plants.

EXAMPLE 1

Identification of the aba4-1 Mutant

The aba4-1 mutant was isolated from the Institut National de la Recherche Agronomique Versailles T-DNA collection (BECHTOLD et al., C.R. Acad. Sci., 316, 1194-1199, 1993) in the Ws-2 background. The plants were screened for their ability to germinate and develop on the GA biosynthesis inhibitor paclobutrazol. Pools of 100 T3 or T4 lines were sown on 0.5% agarose plates containing 100 μM paclobutrazol and incubated in a growth cabinet for 10 days, 16 h light at 20° C./8 h dark at 15° C. Resistant seedlings developing green cotyledons were transferred to solid Gamborg B5 media (Duchefa, The Netherlands) containing 29 mM sucrose and 1 μg/mL GA$_3$ and cultured for a further 6 days in the same environmental conditions before transplanting to soil and growth for seed production in a glasshouse with a minimum photoperiod of 13 hours assured by supplementary lighting. Three successive backcrosses to wild-type were performed with selection for a line lacking the non-linked T-DNA insertion at the first back-cross. This screen allowed the selection of eleven mutants that were able to germinate and develop on paclobutrazol.

Six of these mutants were found to correspond to aba3 mutant alleles.

The remaining 5 mutants were analyzed for ABA content and carotenoid composition.

ABA Content Determination

Rosettes were detached from plants grown in soil in the glasshouse (22° C., minimum 13 hours photoperiod) for 3 weeks and placed for 2 hours under a lamina flow hood for stressed samples then harvested and frozen in liquid nitrogen at the same time as equivalent unstressed rosettes. ABA was extracted from ground freeze-dried rosettes or dry seeds as described previously (NORTH et al., Plant Sci., 169, 115-124, 2005). In each experiment measurements were carried out using tissue from at least three individual plants with five independent assays of each sample; each experiment was repeated three times.

Analysis of Carotenoid Composition

Extractions were carried out using rosette leaves from 3 week old plants grown in soil in the glasshouse (22° C., minimum 13 hours photoperiod). Pigments were extracted in acetone from 6 mm leaf discs and separated by HPLC as described previously (NORTH et al., Plant Sci., 169, 115-124, 2005) Pigments were detected with a photodiode-array detector (Beckman-Coulter, Villepinte, France). Peak identification was based on comparison of retention times and absorption spectra to commercially available standards; zeaxanthin, lutein, β-carotene (Extrasynthèse, Genay, France), chlorophyll a and b (Fluke, Sigma-Aldrich Chimie, St. Quentin Fallavier, France) or published values (BRITTON, UV/Visible spectroscopy. In Carotenoids. Vol 1B: Spectroscopy. G Britton, S Liaaen-Jensen, H Pfander, eds, (Basel: Birkhäuser Verlag), pp. 13-62, 1995).

2 of the 5 mutants showed altered carotenoid compositions on HPLC analysis of leaf extracts. Analysis of the ABA contents of the two mutants confirmed them to be affected in ABA biosynthesis as ABA levels were reduced in both leaves and seeds.

One mutant presented an accumulation of zeaxanthin characteristic of aba1 mutants defective for the zeaxanthin epoxidase gene. Sequencing of the ABA1 gene in this mutant identified the insertion of an A 2851 bp into the zeaxanthin epoxidase coding sequence, thus altering the coding sequence for the following 45 amino acids before generating a premature STOP codon; this mutant was thus named aba1-13.

Figure 1:
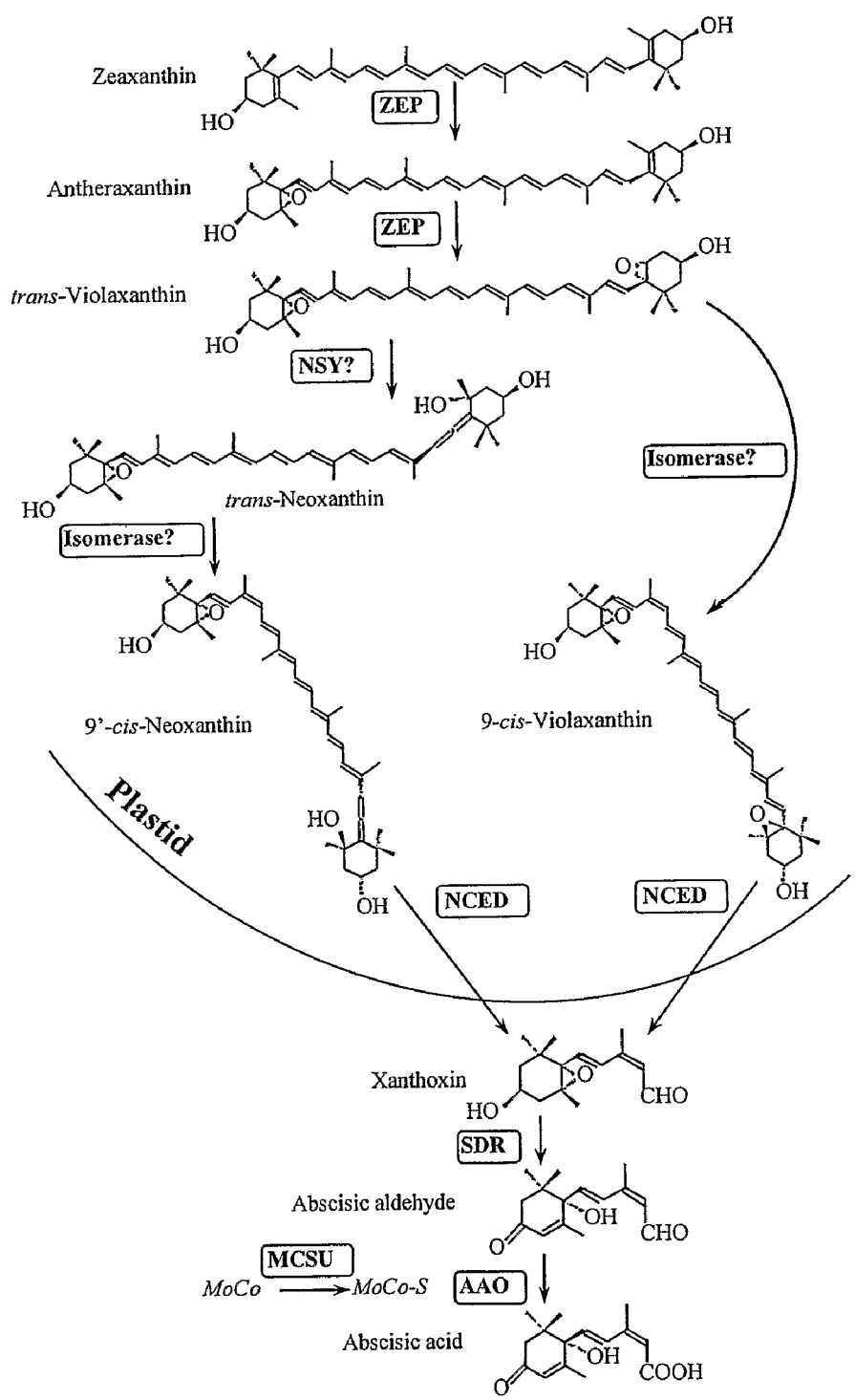
FIG. 1: ABA biosynthesis pathway: ABA is synthesized from C$_{40}$ carotenoid precursors and the pathway shown is from the xanthophyll zeaxanthin onwards. Enzymes responsible for the different reactions are boxed. ZEP, zeaxanthin epoxidase, NSY, neoxanthin synthase, NCED, 9-cis-epoxy-carotenoid dioxygenase, SDR, short chain dehydrogenase/reductase, AAO, abscisic aldehyde oxidase, MCSU, molybdenum cofactor sulfurase. Question marks indicate steps for which enzymes remain to be identified.
Figure 2:
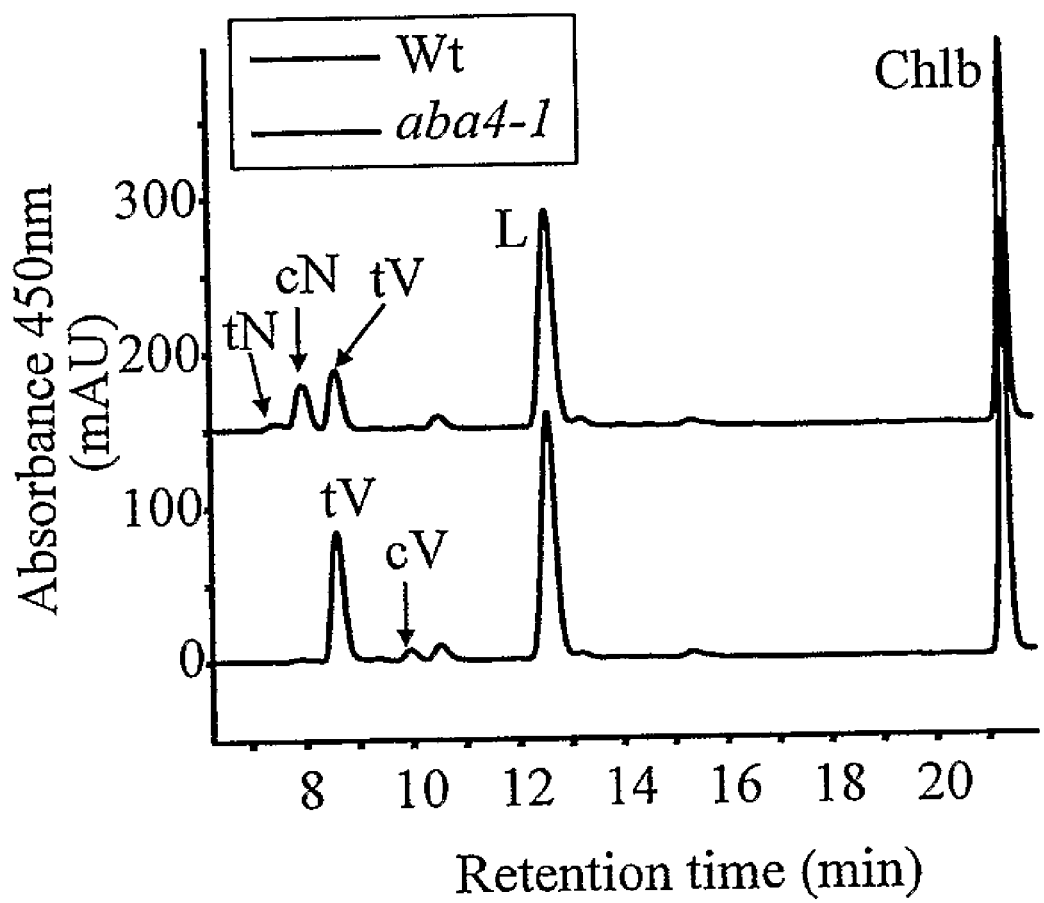
FIG. 2: HPLC profile of wild-type and aba4-1 leaf pigments: tN, trans-neoxanthin, cN, cis-neoxanthin, tV, trans-violaxanthin, L, lutein, Chlb, chlorophyll b.

The HPLC profile of leaf extracts of the second mutant is shown in FIG. 2. Compared to wild-type, extracts from leaves of this mutant accumulated trans-violaxanthin and lacked neoxanthin isomers, indicating that neoxanthin synthesis was affected. No ABA-deficient mutant affected in neoxanthin synthesis has been described to date so the novel locus was called aba4-1.

EXAMPLE 2

Isolation and Characterization of aba4-2 and aba4-3 Mutants

Genetic analysis of the aba4-1 mutant found that it was inherited as a single recessive locus, but that no T-DNA insertion co-segregated with the mutant phenotype (data not shown). Mapping of the mutation using linkage analysis to molecular markers localized the gene to a region on the lower arm of chromosome 1 between nga280 and nga111. Fine mapping reduced the region to a 136 kb interval containing 21 annotated genes. A search of the SIGnAL database (ALONSO et al., Science, 301, 653-7, 2003) was carried out for Salk T-DNA insertion lines within these genes. Homozygous insertion lines corresponding to 9 of the predicted genes were obtained from the Nottingham *Arabidopsis* Stock Centre (NASC) and were analyzed for their leaf carotenoid composition. One line (Salk line N637455, Columbia-0 accession) with an insertion in At1g67080 exhibited the same carotenoid profile as the aba4-1 mutant, as shown in Table I below. This mutant was called aba4-3.

TABLE I

| | Carotenoids (mmol/mol chlorophyll a ± SE). | | | | | | |
|---|---|---|---|---|---|---|---|
| Genotype | Zeaxanthin | Antheraxanthin | t-Violaxanthin | c-Violaxanthin | t-Neoxanthin | c-Neoxanthin | Lutein |
| Wt Ws | 5.3 ± 0.2 | 7.0 ± 0.05 | 37.5 ± 0.8 | 1.0 ± 0.05 | 4.1 ± 0.2 | 35.9 ± 0.7 | 115.7 ± 1.4 |
| aba4-1 | 4.1 ± 0.6 | 8.5 ± 0.7 | 69.7 ± 0.3 | 6.9 ± 0.2 | ND | ND | 122.3 ± 5.8 |
| Wt Col-0 | 10.5 ± 2.8 | 7.7 ± 0.3 | 24.6 ± 1.2 | 1.6 ± 0.1 | 3.3 ± 0.1 | 31.7 ± 0.6 | 120.6 ± 2.7 |
| aba4-3 | 8.1 ± 0.4 | 10.5 ± 0.8 | 50.3 ± 2.0 | 5.6 ± 0.1 | ND | ND | 122.9 ± 4.1 |

Values shown are means of 3 individual measurements.
ND, not detectable

A further homozygous insertion line in At1g67080 was obtained from the Versailles T-DNA mutant collection FlagDB/FST (SAMSON et al., Nucleic Acids Res, 30, 94-7, 2002) and this also showed the modified carotenoid profile on HPLC analysis (data not shown) and was therefore called aba4-2.

The ABA levels of well watered rosette leaves and dry seeds of aba4-1, aba4-2 and aba4-3 mutants compared to wild-type and aba1 mutants were analyzed. The results are shown in Table II below.

TABLE II

| | ABA content (pmol $g^{-1}$ DW). | |
|---|---|---|
| Genotype | Well-watered rosettes | Dry seeds |
| Wt Ws | 287 ± 26 | 595 ± 24 |
| aba4-1 | 15 ± 12 | 353 ± 14 |
| aba4-2 | 53 ± 30 | 368 ± 17 |
| aba1-13 | 82 ± 28 | 153 ± 12 |
| Wt Col-0 | 260 ± 32 | 491 ± 27 |
| aba4-3 | 272 ± 21 | 211 ± 17 |
| aba1-5 | 84 ± 33 | 57 ± 8 |

Values are means from ≧6 individual measurements ± SE

Both T-DNA insertion mutants showed similar reductions in ABA levels in seeds as the aba4-1 mutant, but only the mutants in the Ws-2 accession showed reduced ABA contents in well watered rosette leaves.

Crosses between the three different mutant lines did not result in genetic complementation, thus confirming that the ABA4 gene corresponded to At1g67080.

EXAMPLE 3

Characterization of the ABA4 Gene and of the Corresponding Protein

Comparison of the ABA4 genomic sequence with that obtained for a full-length ABA4 cDNA available in the RIKEN *Arabidopsis* full-length clone collection allowed the gene structure to be predicted as having six exons and five introns. The deduced polypeptide is predicted to be 220 amino acids in length with the first 68 amino acids presenting the features of a chloroplast signal peptide; rich in hydroxylated amino acids, an alanine residue at position 69 in agreement with the chloroplast transit peptide cleavage-site motif (KEEGSTRA, Cell, 56, 247-53, 1989; GAVEL and VON HEIJNE, FEBS Lett, 261, 455-8, 1990). Furthermore, this protein was identified in a proteomic analysis of proteins present in chloroplast envelope membrane extracts of *Arabidopsis* (FERRO et al., Mol Cell Proteomics, 2, 325-45, 2003). The mature ABA4 protein thus has a predicted molecular mass of 17.0 kDa and a theoretical pI of 7.91. Hydropathy analyses of the putative protein indicate the presence of 4 helical transmembrane domains, but no domains of known function were identified.

Sequencing of the At1g67080 gene in the aba4-1 mutant revealed the insertion of an A in the open reading frame at position 985. The frameshift induced by this insertion changes the following 4 amino acids of the predicted protein, before introducing a STOP codon.

Figure 3:
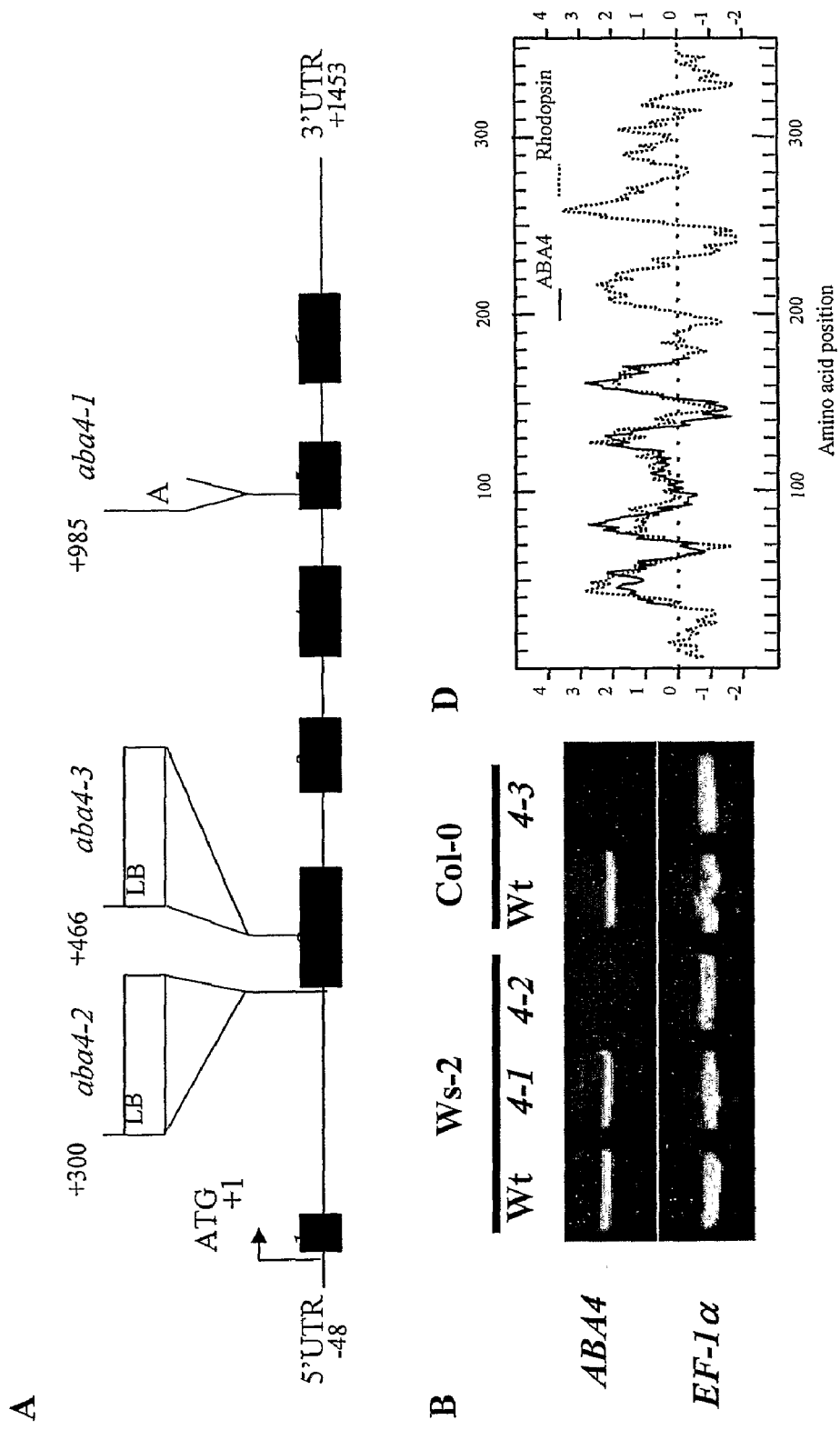
FIG. 3: Structure of the ABA4 gene and putative protein, and characterization of the aba4 mutants.

A schematic representation of ABA4 gene structure and of the relative positions of the aba4 mutant insertions is shown in FIG. 3A. Rectangles indicate the positions of open reading frames.

RT-PCR analysis was performed using primers in exons 3 and 5 of ABA4 (forward primer 5-GGTTTTACCCTTC-TATACTC-3' (SEQ ID NO: 22) and reverse primer 5'-CATTTTAGCTATTCCAGAC-3' (SEQ ID NO: 23). A control experiment was performed with primers for the EF1α-4a gene transcript (forward primer 5'-ATGCCCCAG-GACATCGTGATTTCAT-3' (SEQ ID NO: 24) and reverse primer 5'-TTGGCGGCACCCTTAGCTGGATCA-3' (SEQ ID NO: 25).

The results are shown in FIG. 3B. In agreement with the mutations they contained transcripts were not detectable in aba4-2 and aba4-3, but were present in the aba4-1 mutant.

A BLASTP search identified similar sequences in maize, wheat, rice and cyanobacteria, but the protein appears to be unique in *Arabidopsis* implying that ABA4 is a single copy gene in the genome.

FIG. 3C shows the alignment of the ABA4 predicted amino acid sequences from *Arabidopsis thaliana* (SEQ ID NO: 2), maize ZmABA4a (SEQ ID NO: 4) and ZmABA4b (SEQ ID NO: 6), wheat (SEQ ID NO: 10), and rice (SEQ IN NO: 8).

Sequence alignment was performed using the MultAlin programme (CORPET, Nucl. Acids Res., 16, 10881-10890, 1988) using the Blosum-62-12-2 symbol comparison table. The figure was drawn using Boxshade version 3.21 (HOFMANN, K. and BARON, M. D., http://www.ch.embnet.org/software/BOX_form.html) with a similarity threshold of 50% and the default similarities (FYW, IVLM, RK, DE, GA, TS, NQ).

The higher plants proteins contain a N-terminal region which is not present in the cyanobacterial sequences. The *Arabidopsis*, maize, wheat, and rice proteins do not show any primary sequence similarity over this region, which corresponds to a predicted chloroplast signal peptide.

All of the protein sequences were predicted to contain 4 transmembrane domains. In the higher plant sequences an additional, block of 5 amino acids, four of which are conserved, is found in the putative loop between transmembrane domains 2 and 3, suggesting a function specific to the higher plant protein activity. In addition, a protein kinase C motif (Prosite PDOC00005) was conserved in all the sequences that would result in the phosphorylation of a conserved threonine (T105 in ABA4).

Searches carried out for proteins with a similar hydropathic profile to ABA4 (found that the region corresponding to transmembrane helices 1 to 4 of the rhodopsin apoprotein shares significant structural similarity (FIG. 3D).

Analysis and comparison of the hydrophobicity profiles of the predicted ABA4 mature protein and freshwater eel rhodopsin (Q90215) was performed using the method of KYTE and DOOLITTLE (J Mol Biol, 157, 105-32, 1982). Hydropathy was calculated over a window length of 11 amino acids (DNA strider program, version 1.4 f2).

EXAMPLE 4

Expression Pattern of the ABA4 Gene

ABA4 gene expression in the main tissue types was analyzed by quantitative reverse transcription PCR (QRT-PCR).

Total RNA was prepared from various frozen plant tissues using Sigma mammalian total RNA kit (Sigma-Aldrich, St. Quentin Fallavier, France) following the manufacturer's protocol and including an on column DNase I treatment (RNase-free DNase set, Qiagen, Courtaboeuf, France). Total RNA (2 μg) was used as a template to synthesize first strand cDNA using an oligo(dT) 18 mer primer and the SuperScript first-strand synthesis kit (Invitrogen, Cergy Pontoise, France) according to manufacturer's instructions.

Quantitative real-time PCR reactions were performed using the LightCycler FastStart DNA master SYBR green I kit in a Roche LightCycler 1.0 (Roche Diagnostic, Penzberg, Germany). Reactions used 5 μl of 1:50 diluted sscDNAs in a total volume of 20 μl. Gene specific primers that had been tested for their efficiency rates and sensitivity on dilution series of cDNAs were as follows: ABA4, forward primer 5'-AATGACTCTTGCTTCTGCTTGGAT-3' (SEQ ID NO: 26), reverse primer 5'-GCTTTGGTTACGAAATGC-GAAACGAT-3' (SEQ ID NO: 27); EF1αA4, forward primer 5'-CTTCTTGCTTTCACCCTTGGTGT-3' (SEQ ID NO: 28), reverse primer 5'-TGTCAGGGTTGTATCCGACCTT-3' (SEQ ID NO: 29). The efficiencies of the two primer sets used were almost identical. The reactions were incubated as follows, denaturation of cDNAs and hot start of recombinant Taq DNA polymerase −95° C. for 8 min. then 45 cycles of 95° C. for 10 sec., 59° C. for 4 sec., 72° C. for 9 sec. After the final PCR cycle a fusion curve was obtained to verify the specificity of the PCR amplification by heating at 94° C. for 1 sec, before cooling to 65° C. for 30 sec. Followed by an increase to 94° C. with a temperature transition rate of 0.1° C. S-1.

The results are shown in FIG. 4. Significant levels of transcripts of ABA4 were found in all tissues examined, with slightly higher levels of expression being detected in flowers.

In order to obtain more detailed information about the cell types expressing ABA4, constructs were generated with a 1.7 kb region upstream of the ATG start codon fused to the β-glucuronidase (GUS) reporter gene and transformed into wild-type *Arabidopsis*.

Several independent transformants presented similar GUS transgene expression patterns, although staining intensities varied. Consistent with the QRT-PCR analyses, histochemical staining of transformants found expression in all tissues types examined. In leaves of both plantlets and mature plants staining was extensive with clear expression in vascular tissue as well as trichome cytoplasm. ABA4promoter::GUS expression in roots was more restricted with clear staining of vascular tissue and root hairs. GUS staining in flowers was limited to the sepals, stamens (excluding the pollen) and the stigma below the papillae. In young siliques the staining below the stigmatic papillae was more intense and staining of the pedicel was also observed. As siliques matured the valves became entirely stained with the vascular tissue showing more intense colouring. ABA4promoter::GUS was also expressed throughout the embryo although the future root appeared to be more weakly stained.

EXAMPLE 5

Role of ABA4 in Stress Responses

QRT-PCR analysis of ABA4 expression was carried out on leaf and root tissue from wild-type plants that had been subjected to a rapid dehydration.

For dehydrated tissue, 28 day old plants that had been grown in the greenhouse in a 50:50 mix of standard compost and sand were used. The root system was washed free of growth media and whole plants were placed under a lamina flow hood for 2 hours. Control non-stressed plant material was harvested at the end of the dehydration period. The rosettes and root system of both stressed and control plants were separated and frozen in liquid $N_2$. QRT-PCR was performed as described in Example 4, before dehydration and after dehydration for 2 hours.

The results are shown in FIG. 5A.

Water deficit did not induce any significant change in transcript levels in either roots or leaves.

To determine whether ABA4 expression was nonetheless required for the increase in ABA biosynthesis in response to dehydration, ABA measurements were carried out on dehydrated rosettes of aba4 mutants. ABA content was determined before and after dehydration for 2 hours.

The results are shown in FIGS. 5B and 5C.

In a similar manner to the aba1 mutants, all 3 aba4 mutant alleles showed a marked reduction in ABA accumulation as compared to wild-type (FIGS. 5B and C). This indicates that ABA4 gene expression is important for ABA production. In addition, although the basal ABA levels observed for the aba4-3 mutant were similar to wild-type, the induction of ABA biosynthesis by water deficit was affected suggesting that the absence of effect on basal levels is due to factors related to the Col-0 accession rather than a particularity of the aba4-3 mutation.

To verify that the reduced ABA levels observed in aba4 mutants were indeed important for their response to water deficit, their water loss phenotypes were examined.

Rapid dehydration assays were carried out using 3 week old plants grown in soil in the glasshouse (22° C., minimum 13 hours photoperiod). Four rosettes per genotype were cut from the root system and water loss measured as described previously (NORTH et al., 2005).

The results are shown in FIGS. 6A and 6B.

On rapid dehydration water loss rates in aba4 mutants were higher than those of wild-type, although water loss was less than that of the aba1-5 mutant.

Nine seeds from each genotype were sown on 9 cm×9 cm pots containing a 50:50 (v/v) mixture of sand (2-3 mm particles) and horticultural compost and cultured as described previously (MERLOT et al., Plant J, 30, 601-9, 2002). When plants were 16 days old and watering had been withheld for 3 days.

Thermal images were obtained using a Thermacam PM250 infrared camera (Inframetrics, FLIR Systems, North Billerica, Mass., USA) equipped with a 16° lens exactly as described by MERLOT et al., (2002) cited above.

Visualisation of leaf temperature by infrared thermography permits differences in water loss on progressive dehydration to be distinguished, due to the cooling effect of transpiration on leaf temperature (MERLOT et al., 2002, cited above).

After 3 days of water deficit the leaf temperature of aba4 and aba1 mutants was clearly lower than that of wild-type plants.

These results indicate that the reduced ABA contents found in aba4 mutants are such that responses to both rapid and progressive water deficit are affected.

Mutants affected in ABA biosynthesis in vegetative tissues display sucrose insensitive seedling development (ARENAS-HUERTERO et al., Genes Dev, 14, 2085-96, 2000). This phenotype is related to the involvement of ABA in sugar signalling which induces a postgerminative arrest in wild-type seedlings grown on high sugar concentrations (LOPEZ-MOLINA et al., Proc Natl Acad Sci USA, 98, 4782-7, 2001).

Sucrose sensitivity of seedling development was assayed by sowing surface sterilised seed onto solid Gamborg B5 media (Duchefa Biochemie BV, Haarlem, The Netherlands) supplemented with sucrose in a range of concentrations from 30 mM to 300 mM. Fifty seeds were sown using a sterile scalpel so that spacing between seeds was identical, with 3 repetitions at each concentration. Seeds were stratified at 4° C. for 3 days and then incubated at 20° C. with a 16: 8 hours light/dark photoperiod and a light intensity of 50 µmol m−2 s−1 for 3 weeks. Seedlings that had formed true first leaves were scored as sucrose resistant.

The results are shown in FIGS. 7A and 7B.

In agreement with the reduced levels of ABA in stressed rosette leaves, aba4 mutants showed sucrose resistant development (FIGS. 7A and B). Interestingly, the aba4-3 knock-out mutant in the Col-0 background showed a higher level of resistance than an equivalent knock-out, the aba4-2 mutant in the Ws-2 accession.

It has previously been demonstrated that the expression of the ABA biosynthesis genes AtZEP1, ABA2, AAO3 and ABA3 is induced in seedlings grown on high concentrations of glucose in an ABA dependent manner (CHENG et al., Plant Cell, 14, 2723-43, 2002). To investigate whether similar regulation occurs for the ABA4 gene, QRT-PCR analyses were carried out on seedlings grown on high concentrations of sucrose.

The results are shown in FIG. 7C.

These results indicate that expression of the ABA4 gene is repressed by sucrose in a concentration dependent manner in wild-type of both Ws-2 and Col-0 accessions. Furthermore, in the aba1-13 and aba4-1 mutants repression occurred in a similar manner, although the degree of repression at high sucrose concentrations was less, indicating that although ABA was involved, it was not essential for repression. In addition, in non-stressed seedlings of aba1-13 and aba4-1 the ABA4 transcript levels were lower suggesting that basal levels of ABA have a positive effect on ABA4 gene regulation in the absence of stress or signalling.

EXAMPLE 6

Germination Characteristics of ABA4 Mutants

As described above the aba4-1 mutant was isolated due to its increased paclobutrazol resistance compared to wild-type.

Paclobutrazol resistance has been associated with reduced seed dormancy in other ABA-deficient mutants (LEFEBVRE et al., Plant J, 45, 309-19, 2006).

In order to compare the characteristics of the aba4-1 mutant with those of the aba4 knock-out mutant alleles, paclobutrazol resistant germination was examined over a range of concentrations.

Paclobutrazol resistance and dormancy analyses were carried out as previously described (LEFEBVRE et al., 2006).

The results are shown in FIGS. 8A to 8C.

All of the aba4 mutants showed similar paclobutrazol resistance phenotypes compared to wild-type, although they are less resistant than aba1 mutants. These differences corresponded well with the differences observed in seed ABA content (cf. Table II above).

Analysis of the germination of freshly harvested seeds showed that although aba4-1 mutants are less dormant than wild-type, the effect is much milder than that observed in the aba1-13 mutant (FIG. 8C). Similar differences in paclobutrazol resistance and dormancy phenotypes have been observed for the nced6 and nced9 mutants (LEFEBVRE et al., 2006) and indicate that the reduction of ABA levels in aba4 mutants is close to the threshold required for dormancy induction, whereas the levels are sufficiently low to counteract the effect of paclobutrazol inhibition of GA biosynthesis.

into *E. coli* strain DH10B. After confirming the integrity of the ABA4 fragment by sequencing, transfer to the binary vector pMDC32 (CURTIS and GROSSNIKLAUS, Plant Physiol, 133, 462-9, 2003), containing a dual 35S promoter, was carried out using LR clonase (Invitrogen, Cergy Pontoise, France) according to manufacturer's instructions. The resulting plasmid was introduced into *A. tumefaciens* C58C1pMP9D by triparental mating as previously described (MARIN et al. 1996).

Stable transformation of wild type Col-0 and Ws-2 accessions was carried out using the floral dip method (CLOUGH and BENT, Plant J, 16, 735-43, 1998) and selecting hygromycin resistant transformants. Homozygous hygromycin resistant plants were selected in the progeny of primary transformants, which exhibited a 3:1 segregation for hygromycin resistance. Compared to wild type, water loss was reduced in detached rosettes for 5 transgenic lines among 9 tested in the Ws-2 accession (FIG. 9A) and in all 4 lines tested in the Col-0 accession (FIG. 9B). This indicates that constitutive expression of ABA4 gene enhances plant tolerance to water deficit. Furthermore, increased tolerance to water deficit correlated with higher neoxanthin contents in leaves of transgenic plants, as shown in Table III below.

TABLE III

| Genotype | Total (Z + A + V + N) mmol/mol chlorophyll a | Carotenoid % (Z + A + V + N) | | | | | |
|---|---|---|---|---|---|---|---|
| | | Zeaxanthin | Antheraxanthin | t-Violaxanthin | c-Violaxanthin | t-Neoxanthin | c-Neoxanthin |
| Wt Col-0 | 79.9 ± 1.6 | 13.3 ± 3.3 | 9.7 ± 0.4 | 31.0 ± 1.8 | 2.0 ± 0.2 | 4.2 ± 0.1 | 40.0 ± 1.4 |
| 35S::ABA4 #7 | 80.7 ± 2.6 | 9.9 ± 2.9 | 6.2 ± 0.2 | 31.0 ± 1.2 | 3.7 ± 0.2 | 7.0 ± 0.1 | 42.2 ± 1.6 |
| 35S::ABA4 #11 | 79.1 ± 0.7 | 5.7 ± 0.5 | 6.7 ± 0.3 | 33.4 ± 1.4 | 3.3 ± 0.2 | 6.2 ± 0.2 | 44.6 ± 0.8 |
| 35S::ABA4 #15 | 85.6 ± 2.1 | 9.6 ± 2.0 | 5.7 ± 0.1 | 33.3 ± 1.7 | 3.0 ± 0.2 | 5.9 ± 0.1 | 42.4 ± 0.2 |
| 35S::ABA4 #16 | 79.4 ± 1.7 | 5.1 ± 1.3 | 5.4 ± 0.4 | 32.9 ± 1.1 | 4.3 ± 0.2 | 7.9 ± 0.1 | 44.4 ± 0.4 |

Values shown are means and standard errors of 3 individual measurements

This indicates that constitutive expression of ABA4 gene results in increased neoxanthin synthesis.

EXAMPLE 7

Overexpression of ABA4 in *Arabidopsis*

A genomic fragment containing the ABA4 gene from 9 bp before the ATG to 183 bp after the STOP (corresponding to position 170 to the end of SEQ ID NO: 1) was amplified using the proofreading Pfu Ultra DNA polymerase (Stratagene, Amsterdam, The Netherlands) and the following primers containing partial GATEWAY™ (Invitrogen, Cergy Pontoise, France) B1 or B2 recombination site sequences, forward 5'-AAAAAAGCAGGCTATTTGAATCA-GAGATGGG-3' (SEQ ID NO: 30), reverse 5'-AAGAAAGCTGGGTCAGGAGGTTTTCAAGTTGC-3' (SEQ ID NO: 31). A second PCR was then carried out using primers B1, 5'-GGGGACAAGTTTGTACAAAAAAGCAG-GCT-3' (SEQ ID NO: 32), and B2, 5'-GGGGACCACTTTG-TACAAGAAAGCTGGGT-3' (SEQ ID NO: 33) and Taq DNA polymerase (Eurobio, Les Ulis, France). The resulting PCR product was then recombined into vector pDONR207 (Invitrogen, Cergy Pontoise, France) using BP clonase according to the manufacturer's instructions and transformed

EXAMPLE 8

Overexpression of ABA4 in Maize

Maize plants were transformed with a sequence encoding an ABA4 polypeptide in order to increase their tolerance to water deficit.

A synthetic ZmA2A4 sequence (SynABA4-ZmMod) codon optimised for a higher expression in maize was constructed. This sequence is shown under SEQ ID NO: 34. It encodes a ZmABA4 protein with 100% identity to the native ZmABA4a protein (SEQ ID NO: 4). The SynABA4-ZmMod coding sequence was cloned as an NcoI/NotI fragment, into the entry vector pENTR4 (Invitrogen), cut by NcoI and NotI. The resulting entry clone is named pBIOS1286. The fragment of pBIOS1286 containing SynABA4-ZmMod was then transferred into the plant binary GATEWAY® Destination vector pBIOS886 by in vitro recombination using the Gateway LR Clonase™ II enzyme mix (Invitrogen). The destination vector pBIOS886 is a derivative of pSB11 (KOMARI et al., Plant J. 10, 165-174, 1996) containing selectable marker genes for selection of maize transformants, a constitutive CsVMV promoter (VERDAGUER et al. Plant Mol Biol 6, 1129-1139, 1996) followed a rice Actin intron (MCELROY et al., Plant Cell, (2) 163, 1990), a GATEWAY® cassette, and a Sac66 polyadenylation sequence (JENKINS et al., Plant Cell Environ. 22, 159-167, 1999). The resulting expression vector, named pBIOS1290, is shown in FIG. 10. It expresses SynABA4-ZmMod under the control of the CsVMV promoter.

pBIOS1290 was transferred into Agrobacteria LBA4404 (pSB1) according to KOMARI et al. (1996, cited above) and the maize cultivar A188 was subsequently transformed with this agrobacterial strain as described by ISHIDA et al. (1996, cited above).

It is also possible to obtain a similar construct encoding ZmABA4a by use of a coding sequence derived from SEQ ID NO:3, and a similar construct encoding ZmABA4b by use of a coding sequence derived from SEQ ID NO:5, and to use any of these constructs to transform maize plants, as described above.

Transgenic lines were characterized by Southern Blot and their progeny by Q-PCR to confirm the copy number. The transgene expression was confirmed by RT-PCR. Transgenic lines were cultivated in greenhouse, under irrigation conditions.

Several transgenic lines were tested for their carotenoid content by HPLC analysis, and for their loss of water under dessication conditions.

The results of HPLC analysis are shown in FIG. 11. Some of the transgenic lines have a high content in carotenoids (see transgenic lines 2 and 11 on FIG. 11a), particularly in trans-violaxanthin (FIG. 11b) and in cis-neoxanthin (FIG. 11c); the quantity of these carotenoids appears to depend on the number of copies of the transgene. The cis-violaxanthin content is constant (FIG. 11d).

Dessication experiments were performed on plants presenting five leaves. The mature (ligulated) leaf number 3 was cut, weighed and placed under laminar bench flow, then weighed regularly to evaluate the water loss.

The results observed on one of the transgenic lines tested are shown on FIG. 12. These results show that the transgenic plants overexpressing ABA4 lose less water that the non transgenic plants.

These results show that overexpression of ABA4 results in a higher content in trans-violaxanthin and cis-neoxanthin, and in a better resistance to dehydration.

The invention claimed is:

1. A method for increasing the tolerance of a plant to water deficit, said method comprising:
   i) introducing into said plant said plant nucleic acid encoding an ABA4 polypeptide comprising the following regions:
      a) a chloroplast signal peptide;
      b) a region having at least 95% identity with the region 83-235 of the polypeptide of SEQ ID NO: 4,
         wherein said region b) comprises the following sequence:
         QIASX$_1$X$_2$FX$_3$X$_4$GTX$_5$AVLPFYTLMX$_6$X$_2$APX$_{17}$AX$_{18}$X$_6$TKX$_{16}$X$_{19}$X$_{20}$X$_{21}$SX$_7$X$_2$PYX$_6$X$_8$LGX$_9$LYX$_2$YLLYX$_{10}$SWTPX$_{21}$TX$_{10}$X$_{16}$X$_{22}$MFX$_{23}$SKYX$_{15}$LPELX$_{24}$GIX$_2$X$_{16}$MFX$_{23}$SEMTX$_{11}$ASAWIHLLX$_2$VDLFAARQVYX$_{25}$DGX$_{10}$X$_{26}$NX$_{27}$X$_6$ETRHSVSLCLLFCPX$_6$GIX$_{12}$X$_{13}$HX$_{14}$X$_{11}$TK
         (SEQ ID NO: 16) wherein X$_1$=S or C, X$_2$=V or A, X$_3$=A or T, X$_4$=V, L or W, X$_5$=T, V or I, X$_6$=V or I, X$_7$=S, G or T, X$_8$=I or A, X$_9$=V, L or I, X$_{10}$=I or L, X$_{11}$=L or V, X12=V, L or A, X$_{13}$=A, T, or S, X$_{14}$=V, A or F, X$_{15}$=M or W, X$_{16}$=R or K, X$_{17}$=K or N, X$_{18}$=E, D, or S, X$_{19}$=C, T, or A X$_{20}$=M or V, X$_{21}$=E or D, X$_{22}$=A or Y, X$_{23}$=A or S, X$_{24}$=S, P, A, or T, X$_{25}$=H, N, or Q, X$_{26}$=K, R, or E, X$_{27}$=Q or N; and
   ii) selecting for a plant having increased tolerance to water deficit compared to a corresponding non-transformed control plant.

2. The method of claim 1, wherein the chloroplast signal peptide of said ABA4 polypeptide is
   a peptide having the following sequence:

(SEQ ID NO: 18)
   MAPCASPSALALSASTRVSSFPLTLRPRPRPEARVPRAPGGAQLRPATACSWPRPLLPELAPAFPRAGARSAGRPQPLFRPR

3. The method of claim 1, wherein said ABA4 polypeptide comprises SEQ ID NO: 4.

4. A recombinant DNA construct comprising a polynucleotide encoding an ABA4 polypeptide comprising SEQ ID NO: 4, under the control of a promoter.

5. An expression cassette comprising the DNA construct of claim 4.

6. An expression vector comprising the DNA construct of claim 4.

7. A host cell comprising the recombinant DNA construct of claim 4.

8. The host cell of claim 7, wherein said host cell is a plant cell.

9. A transgenic plant containing a transgene comprising the DNA construct of claim 4.

10. A method for producing a transgenic plant having an increased tolerance to water deficit, when compared to a non-transgenic plant, said method comprising the steps of:
    transforming at least one plant cell with a vector containing the expression cassette of claim 5;
    cultivating said transformed plant cell in order to regenerate a plant containing in its genome a transgene comprising said expression cassette; and
    selecting for a plant having increased tolerance to water deficit as compared to a corresponding non-transformed control plant.

11. A host cell comprising the expression cassette of claim 5.

12. A host cell comprising the expression vector of claim 6.

13. A transgenic plant containing the expression cassette of claim 5.

14. A plant having increased tolerance to water deficit produced from the method of claim 1.

* * * * *